US012697142B2

(12) United States Patent
Kraus et al.

(10) Patent No.: US 12,697,142 B2
(45) Date of Patent: Aug. 4, 2026

(54) CONNECTING APPARATUS FOR CONNECTING PINS AND/OR ROD ELEMENTS OF AN EXTERNAL FIXATOR, EXTERNAL FIXATOR, AND DEVICE FOR OUTPATIENT EMERGENCY CARE

(71) Applicants: Kilian Kraus, Werneck (DE); Andreas Rutencrantz, Neukirchen-Vluyn (DE)

(72) Inventors: Kilian Kraus, Werneck (DE); Andreas Rutencrantz, Neukirchen-Vluyn (DE)

( * ) Notice: Subject to any disclaimer, the term of this patent is extended or adjusted under 35 U.S.C. 154(b) by 645 days.

(21) Appl. No.: 17/996,317

(22) PCT Filed: Apr. 15, 2021

(86) PCT No.: PCT/EP2021/059791
§ 371 (c)(1),
(2) Date: Aug. 18, 2023

(87) PCT Pub. No.: WO2021/209554
PCT Pub. Date: Oct. 21, 2021

(65) Prior Publication Data
US 2024/0188993 A1 Jun. 13, 2024

(30) Foreign Application Priority Data

Apr. 15, 2020 (EP) ..................................... 20169721
Apr. 15, 2020 (EP) ..................................... 20169722

(51) Int. Cl.
*A61B 17/64* (2006.01)
*A61B 17/84* (2006.01)

(52) U.S. Cl.
CPC ........ *A61B 17/6483* (2013.01); *A61B 17/846* (2013.01)

(58) Field of Classification Search
CPC .............. A61B 17/6483; A61B 17/846; A61B 17/6466; A61B 17/64; A61B 17/6491;
(Continued)

(56) References Cited

U.S. PATENT DOCUMENTS 4,159,716 A * 7/1979 Borchers ............ A61B 17/1697
606/104
4,653,481 A 3/1987 Howland et al.
(Continued)

FOREIGN PATENT DOCUMENTS

EP 2588013 A1 5/2013
RU 2606269 C2 1/2017
WO 2015/066044 A1 5/2015

OTHER PUBLICATIONS

European Search Report as received in EP application 20169722.4 dated Oct. 2, 2020.
(Continued)

*Primary Examiner* — Eduardo C Robert
*Assistant Examiner* — Tara Rose E Carter
(74) *Attorney, Agent, or Firm* — Keller Preece PLLC

(57) ABSTRACT

The invention relates to a connecting apparatus for the purpose of connecting pins and/or rod elements of an external fixator, having a first clamping arrangement for fastening at least one pin and/or rod element and a second clamping arrangement for fastening at least one pin and/or rod element, the first and second clamping arrangements being mounted to be rotatable relative to each other via a rotary joint about an axis of rotation and to be pivotable relative to each other via a pivot joint about a pivot axis which runs perpendicular to the axis of rotation. A traction means which can be subjected to a tensile load is guided through the first and second clamping arrangements, the rotary joint and the pivot joint. The invention also relates to an external fixator, having at least one such connecting apparatus and a device for ambulatory emergency care comprising an external fixator.

29 Claims, 13 Drawing Sheets

(58) Field of Classification Search
 CPC ..... A61B 17/66; A61B 17/663; A61B 17/666;
 A61B 17/68; A61B 17/681
 USPC .............................................. 606/53–59, 104
 See application file for complete search history.

(56) References Cited

U.S. PATENT DOCUMENTS

| | | | | |
|---|---|---|---|---|
| 5,979,658 | A | * | 11/1999 | Allen ...................... A61F 17/00 |
| | | | | 206/229 |
| 6,110,173 | A | * | 8/2000 | Thomas, Jr. ....... A61B 17/7052 |
| | | | | 606/252 |
| 8,147,490 | B2 | | 4/2012 | Bauer |
| 2007/0049930 | A1 | * | 3/2007 | Hearn ................... A61B 17/66 |
| | | | | 606/56 |
| 2011/0245833 | A1 | | 10/2011 | Anderson |
| 2012/0089142 | A1 | | 4/2012 | Mullaney et al. |
| 2012/0296335 | A1 | * | 11/2012 | Mullaney ........... A61B 17/6466 |
| | | | | 606/59 |
| 2017/0181774 | A1 | * | 6/2017 | Cahill ................ A61B 17/7082 |
| 2017/0360525 | A1 | * | 12/2017 | Brown ...................... B65B 7/00 |
| 2019/0223923 | A1 | | 7/2019 | Cahill |
| 2020/0069349 | A1 | | 3/2020 | Lavi et al. |

OTHER PUBLICATIONS

European Search Report as received in EP application 20169721.6 dated Oct. 2, 2020.

* cited by examiner

CONNECTING APPARATUS FOR CONNECTING PINS AND/OR ROD ELEMENTS OF AN EXTERNAL FIXATOR, EXTERNAL FIXATOR, AND DEVICE FOR OUTPATIENT EMERGENCY CARE

CROSS-REFERENCE TO RELATED APPLICATIONS

This application is a national phase entry under 35 U.S.C. § 371 of International Application No. PCT/EP2021/059791, filed Apr. 15, 2021, which claims the benefit of European Patent Application No. 20169721.6, filed Apr. 15, 2020 and European Patent Application No. 20169722.4, filed Apr. 15, 2020. The foregoing applications are incorporated by reference in their entirety.

BACKGROUND OF THE INVENTION

1. Field of the Invention

The invention relates to a connecting apparatus for the purpose of connecting pins and/or rod elements of an external fixator, to an external fixator having at least one such connecting apparatus, and to a device for ambulatory emergency care comprising an external fixator and at least one connecting apparatus.

2. Background and Relevant Art

The connecting apparatus comprises a first clamping arrangement for fastening at least one pin and/or rod element and a second clamping arrangement for fastening at least one pin and/or rod element. The first and second clamping arrangements are mounted to be rotatable relative to each other via a rotary joint about an axis of rotation, and pivotable relative to each other via a pivot joint about a pivot axis running perpendicular to the axis of rotation.

An external fixator is an apparatus for stabilizing and immobilizing a fracture, and is typically used by first responders, in particular at the location where the injury occurred, in order to achieve at least temporary fixation of the fracture, and thus, for example, make the injured person fit to be transported.

External fixators generally comprise a plurality of components which can be connected or coupled to each other in order to achieve the stabilization mentioned above. An external fixator typically includes a number of rod-shaped pins which, for example, have drilling screw threads and are designed to be driven into the bone parts to be fixed. Such pins can in particular be designed as so-called Steinmann pins or Schanz screws. The pins, which are driven into the bone tissue percutaneously, are connected to each other comparatively rigidly via a manner of linkage outside the body, such that the bone parts cannot move relative to each other—or only to a small extent. As a rule, stabilizing elements are used to connect the pins, which elements have, for example, an elongate, rod-shaped, or curved shape, and are designed to be connected to each other and/or to the pins by means of connecting apparatuses. The number, type, location and orientation of the components used to stabilize the bone fracture usually depend on the type of injury. In the case of comparatively simple fractures, adequate fixation of the bone parts can sometimes be achieved by connecting the pins driven into the corresponding bone parts via a single rod or via a single stabilizing element that bridges the fracture site.

In the case of more complicated fractures, or in particular in the case of fractures which require the bridging of a joint of the injured person, provision can be made, for example, for several stabilizing elements to be coupled to each other in order to achieve adequate fixation.

External fixators (also called pin fixators) are used, for example, in the case of closed or open fractures of the extremities, in particular in cases where soft tissue has been injured. A temporary fixation of such fractures by means of an external fixator is particularly indicated in cases in which the injured person has other, more life-threatening injuries, the care of which has a higher priority from a medical point of view. Typically, in such cases, the fracture is provisionally reduced with subsequent fixation in the manner already described using an external fixator after the condition of the injured person has been stabilized, for example as part of emergency procedures. The final treatment and stabilization of the fracture, for example by means of a plate, screw or nail, as part of the so-called definitive treatment, usually only takes place once the patient's condition allows it. This may take a few hours, but usually takes a day or several days, or even a week.

The risk of infection at the implant is particularly high in the case of higher-grade open fractures. In the case of such fractures, primary care is preferably provided by means of external fixators in order to prevent infection. The actual osteosynthesis typically takes place in such delayed cases after a few days by means of implants such as plates, screws or nails.

The application and assembly of an external fixator is a relatively complex process. In emergency situations in particular, however, it is extremely advantageous if the fixation and stabilization of fractures by means of such external fixators take place as promptly as possible, such that the patient's fitness for transport can be achieved as quickly as possible. A construction that is easy to grasp intuitively, and an assembly of the fixator that is easy to understand intuitively, are therefore extremely advantageous and accordingly desirable.

A device for ambulatory emergency care includes the following components:

an external fixator, having at least two, for example four, pins which are designed for anchoring, in particular by screwing, into bone tissue, at least one rod element, and at least one connecting apparatus, in particular at least two, for example three connecting apparatuses, which are designed to mechanically connect at least one of the pins to the at least one rod element.

Medical devices having a number of components, which are used to carry out medical procedures, in particular as part of emergency care, are known from the prior art. For example, first-aid kits contain various medical devices and dressing materials which, when used as intended, are suitable for treating smaller and larger, in particular open, wounds.

A medical device for performing a surgical intervention is known from WO 2014 083 526 A1. In the manner of a surgical kit, the device has a plurality of sterilized or sterilizable components which are organized in a specific manner on a base. The base is equipped with printed illustrations and/or information intended to explain the intended use of the components during surgical procedures. In this way, in particular, possible errors that could be caused by inexperienced, insufficiently trained medical personnel, or as the result of negligence, should be avoided.

BRIEF SUMMARY OF THE INVENTION

The object of the invention is to specify a connecting apparatus and an external fixator which can be assembled particularly quickly and easily when required. The object of the invention is also to specify a device for ambulatory emergency care, having an external fixator which allows immediate medical procedures to be carried out with reduced requirements for personnel.

With regard to the connecting apparatus, this object is achieved by a connecting apparatus for the purpose of connecting pins and/or rod elements of an external fixator, having the features of claim 1, with regard to the external fixator by the features of claim 16, and with regard to ambulatory emergency care by the features of claim 18.

Advantageous designs are the subject matter of the respective dependent claims.

A connecting apparatus for the purpose of connecting pins and/or rod elements of an external fixator comprises a first clamping arrangement for fastening at least one pin and/or rod element and a second clamping arrangement for fastening at least one pin and/or rod element. The first and second clamping arrangements are rotatable relative to each other via a rotary joint about an axis of rotation, and pivotable relative to each other via a pivot joint about a pivot axis running perpendicular to the axis of rotation. According to the invention, a tension-loadable traction means is passed through the first and second clamping arrangement, the rotary joint, and the pivot joint. The tension-loadable traction means is designed to fix the first and second clamping arrangement in place by imparting a tensile force (or: tensile stress, tensile load) in the axial direction along the traction means, and to lock them in different angular positions with respect to the axis of rotation and the pivot axis.

The traction means has, in particular, an elongated shape that extends in the axial direction and is, for example, designed as a single piece—or is at least designed to be rigid. The axial direction is specified in particular by the longitudinal extension of the traction means. Since the one-piece, or rigid, traction means is passed through both the first and the second clamping arrangement, and also the rotary joint and the pivot joint, all degrees of freedom of the connecting apparatus can be fixed by imparting a tensile force in the axial direction along the traction means. On the one hand, these degrees of freedom relate to the rotations of the clamping arrangements relative to each other about the pivot axis and about the axis of rotation. On the other hand, the rod elements and/or pins in the clamping arrangements are fastened in a non-positive manner by the provision of the tensile force in the axial direction along the traction means. For this purpose, the first clamping arrangement and the second clamping arrangement have, for example, first and second clamping jaws that can be braced against each other. To completely fix and lock the connecting apparatus, it is only necessary to provide a tensile stress acting along the traction means; this can be done, for example, by tightening a single adjusting means, such as an adjusting screw or a screw nut. The effort required to operate and apply an external fixator having such connecting apparatuses is therefore reduced. In addition, the functionality of the external fixator is particularly easy to grasp intuitively, such that it can also be applied by a person who has not been medically trained or is at least comparatively inexperienced, in particular as part of an emergency medical procedure.

In certain configurations, the traction means is designed, for example, as a screw. In such embodiments, the axial direction corresponds to the direction in which the longitudinal center axis of the screw is oriented. In general, the axial direction differs from the direction of the pivot axis because the orientation of the axis of rotation depends on the angular position of the clamping arrangements about the pivot axis. In a starting position, in which the clamping arrangements are not displaced relative to each other with respect to the pivot axis, the axis of rotation runs coaxially with the axial direction, which is substantially defined by the longitudinal extension of the traction means.

In certain configurations, the rotary joint comprises at least two adjacent rotary joint components which are mounted such that they can rotate relative to each other about the axis of rotation, and which can be locked in different angular positions relative to each other by means of the traction means. A first spring means is arranged between the rotary joint components, and is designed to brace the rotary joint components away from each other in the axial direction. The traction means is guided, for example, centrally through the rotary joint components that form the rotary joint. The first spring means produces a spring force acting in the axial direction, which spring force is designed to drive the rotary joint components apart, such that they can be moved with respect to each other into the desired angular position, in particular by hand, in the unloaded state in which the traction means is not or is only slightly under tensile load. By creating the tensile force in the axial direction along the traction means, the rotary joint components can then be locked in the desired angular position—that is, the tensile load acting to lock the connecting apparatus is oriented against the spring force created by the first spring means.

In certain configurations, the first spring means is designed, for example, in the form of a wave spring. In certain configurations, the first spring means can, for example, have rings or ring elements arranged concentrically to each other and around the axial axis A, which are connected to each other via axially running webs. The first spring means is preferably designed to absorb forces occurring in the axial direction and transversely, which forces act on the rotary joint or on the rotary joint components, for example, in directions that deviate from the direction in which the axis of rotation is oriented. For this purpose, in certain configurations, the first spring means is designed as a cylinder beam spring that can withstand bending loads or is subjected to bending loads. The first spring means can be made of titanium or aluminum, for example, or can comprise titanium or aluminum.

The first spring means can be designed as a separate component of the connecting apparatus. In advantageous configurations, the first spring means is formed as a single piece with one of the rotary joint components. In certain configurations, the first spring means can have a ring element, for example, which is connected to one of the rotary joint components via webs. Furthermore, the spring element is preferably designed to additionally guide and center the two rotary joint components. For this purpose, the spring means projects, in particular in the axial direction A, beyond the rotary joint component, or protrudes at least partially from it in the axial direction A.

Together with the traction means which is guided centrally through the rotary joint components, the mutually adjacent rotary joint components substantially implement the functionality of the rotary joint, i.e., the rotation of the first and second clamping arrangements relative to each other and about the axis of rotation. In certain configurations in which the traction means is guided centrally through the rotary joint components, these can be rotated relative to each other and about the traction means, preferably through an angular range of 360°.

In certain configurations, the rotary joint components are, for example, substantially disk-shaped and arranged opposite each other on the end faces.

In certain configurations, the first clamping arrangement is connected to one of the rotary joint components and the second clamping arrangement is connected to the other rotary joint component in a rotationally fixed manner, at least with respect to a rotation about the axis of rotation. In certain configurations, at least one of the rotary joint components is implemented as an integral part of the first or second clamping arrangement. For example, at least one of the rotary joint components forms a (first or second) clamping jaw of the first or second clamping arrangement. In other words, in certain configurations, at least one of the rotary joint components can be formed as a single piece together with a (first or second) clamping jaw of the first and/or second clamping arrangement, for example. In this way, the number of components required to form the connecting apparatus can be reduced, and weight can thus be saved in particular. This is particularly advantageous when the external fixator presented here is used in the field of civil protection and/or the military, since it may be necessary in such cases to carry the external fixator as part of emergency medical equipment in the field, especially over longer distances.

In certain configurations, the rotary joint components have first surface structures which are arranged opposite each other and are designed to be complementary to each other, designed to engage in each other with a positive connection in different angular positions. Correspondingly, the rotational degree of freedom of the connecting apparatus is locked in relation to the movement of the clamping arrangements about the axis of rotation with the additional aid of a positive connection. In this way, the force required to lock this degree of freedom can be significantly reduced compared to designs that are based exclusively on a non-positive and/or frictional locking, and the mechanical stability of the mounted external fixator can be improved. In particular, it can be achieved that the tensile load required for adequately fixing the components connected by means of the connecting apparatus can be created by a person without tools and/or manually, for example by tightening a single adjusting means that is in an operative connection with the traction means. This adjusting means is, for example, a hand wheel, a star knob, a screw or a screw nut which is in an operative connection with the traction means to create the tensile load.

In certain configurations, the first surface structure has, for example, a toothed or corrugated structure, at least in regions thereof. In certain configurations, the first surface structures are designed, for example, as circumferential crown teeth that protrude axially in the direction of the axis of rotation, and which are arranged opposite each other and are designed as spur gear teeth to engage in each other with a positive connection.

In certain configurations, the pivot joint comprises at least two adjoining pivot joint components which are mounted such that they can pivot relative to each other about the pivot axis, and which can be locked in different angular positions relative to each other by means of the traction means. A second spring means is arranged between the pivot joint components, and is designed to brace the pivot joint components away from each other in the axial direction. The traction means is guided, for example, centrally through the pivot joint components that form the pivot joint. The second spring means produces a spring force acting in the axial direction, which spring force is designed to drive the pivot joint components apart, such that they can be moved with respect to each other into the desired angular position, in particular by hand, in the unloaded state in which the traction means is not or is only slightly under tensile load. By creating the tensile force in the axial direction along the traction means, the pivot joint components can then be locked in the desired angular position—that is, the tensile load acting to lock the connecting apparatus is oriented against the spring force created by the second spring means.

In certain configurations, the second spring means is designed as a leaf spring, for example. In certain configurations, the leaf spring has a centrally arranged opening through which the traction means is guided.

Together with the traction means which is guided centrally through the pivot joint component, the mutually adjacent pivot joint components substantially implement the functionality of the pivot joint, i.e., the rotation of the first and second clamping arrangements relative to each other and about the pivot axis. In certain configurations, the pivot joint components are pivotable relative to each other through a limited angular range of less than 180°, in particular through an angular range of less than 90°. In certain configurations, the pivot joint components and/or the first clamping arrangement are/is pivotable relative to the second clamping arrangement through an angular range of at least 40°, for example in an angular range of approximately +/−20°, relative to a starting position.

In certain configurations, at least one of the pivot joint components has a central elongated hole through which the traction means is guided. The elongated hole forms a kind of slotted link along which the centrally guided traction means can be moved, such that the two clamping arrangements can be moved relative to each other about the pivot axis over a correspondingly large angular range.

The pivot joint components are, for example, substantially disk-shaped, and are arranged opposite each other. The oppositely arranged sides of the pivot joint components have, for example, at least partially curved portions which restrict the movement of the two pivot joint components relative to each other substantially to a pivot movement perpendicular to the axis of rotation. The mutually facing sides of the pivot joint components are shaped, for example, in such a way that the pivot joint components cannot be moved relative to each other about the axis of rotation. In other words, the pivot joint components in such configurations form, together with the traction means, a pivot joint which connects the first clamping arrangement to the second clamping arrangement in a rotationally fixed manner with regard to rotations about the axis of rotation.

In certain configurations, the first clamping arrangement is connected in a rotationally fixed manner to one of the pivot joint components, and the second clamping arrangement is connected in a rotationally fixed manner to the other pivot joint component—at least with respect to rotation about the pivot axis. In certain configurations, at least one of the pivot joint components is implemented as an integral part of the first or second clamping arrangement. For example, at least one of the pivot joint components forms a (first or second) clamping jaw of the first or second clamping arrangement. In other words, it is provided in certain configurations, for example, for at least one of the pivot joint components to be designed as a single piece together with a (first or second) clamping jaw of the first or second clamping arrangement. In this way, too, the number of components required to form the connecting apparatus can be reduced, and accordingly, in particular, weight and/or material costs can be saved.

In certain configurations it is provided that the function of one of the pivot joint components and the function of one of the rotary joint components is realized by a single component. Accordingly, this component acts both as a rotary and as a pivot joint component in order to further reduce the number of components required to implement the connecting apparatus. The rotary joint and the pivot joint are formed, in certain configurations, for example, by only three components, which are substantially disk-shaped and which adjoin each other in succession in the axial direction, and provide a connection between the first and the second clamping arrangement in such a way that they can be positioned in different angular positions relative to each other, both with regard to the pivot axis and to the axis of rotation. In certain configurations in which (first or second) clamping jaws of the first and/or the second clamping arrangement also function as rotary joint or pivot joint components, the number of components is reduced even further. In this way, the installation space required to implement the connecting apparatus is reduced in the axial direction and additional weight is saved.

In certain configurations, the pivot joint components have second surface structures which are arranged opposite each other and are designed to be complementary to each other, and are designed to engage in each other with a positive connection in different angular positions. Correspondingly, the rotational degree of freedom of the connecting apparatus is locked in relation to the movement of the first and second clamping arrangements about the pivot axis with the additional aid of a positive connection. In this way, the force required to lock this degree of freedom can be significantly reduced compared to designs that are based exclusively on a non-positive and/or frictional locking, and the mechanical stability of the mounted external fixator can be improved. The tensile load required for adequately fixing the components connected by means of the connecting apparatus can be created by a person without tools and/or manually, for example by tightening a single adjusting means that is in an operative connection with the traction means. This adjusting means is, for example, a hand wheel, a star knob, a screw or a screw nut which is in an operative connection with the traction means to create the tensile load.

In certain configurations, the second surface structures have, for example, toothed or corrugated structures, at least in regions. In certain configurations, the second surface structures include, for example, a plurality of grooves, flutings, and/or ridge-like ribs running parallel to the pivot axis. In certain configurations, the ridge-like ribs are designed, for example, to be complementary to the grooves or flutings. In order to provide the positive connection, the ridge-like ribs of one pivot joint component are arranged opposite the grooves or flutings of the other pivot joint component, such that they can engage in each other in the manner of spur gear teeth.

In certain configurations, the first clamping arrangement and/or the second clamping arrangement has/have two opposite first and second clamping jaws that can be braced against each other by means of the tensile force acting in the axial direction, and which each have oppositely arranged first receiving grooves for receiving a rod element. The rod elements (also: rods, posts) of the external fixator can be inserted into the receiving grooves and connected in different spatial configurations by means of the connecting apparatus already described, and can be locked in a non-positive and/or frictional manner by the application of the axial tensile load.

In certain configurations, the first receiving grooves are provided, at least in portions thereof, with third surface structures which are designed to positively engage in complementary surface structures of a rod element. In certain configurations, the third surface structure comprises, for example, a plurality of grooves, flutings, and/or ridge-like ribs running parallel to each other. In such designs, the rod elements are thus fixed with the additional aid of a positive connection, as a result of which significantly greater torsional moments can be transmitted between the connecting apparatus and the rod elements compared to a pure non-positive and/or frictional connection.

In certain configurations, the first clamping arrangement and/or the second clamping arrangement has/have two opposite first and second clamping jaws that can be braced against each other by means of the tensile force acting in the axial direction, and which each have oppositely arranged second receiving grooves for receiving a pin. The pin can be inserted into the receiving grooves of the opposite first and second clamping jaws and locked in a non-positive and/or frictional manner by the application of the axial tensile load. The pin is designed to be driven into the bone tissue of an injured person or a patient, and has a tap thread for this purpose, for example. Typically, the pin is firmly connected to the connecting apparatus after it has been anchored in the bone tissue. In certain configurations, the pins are designed as threaded rods, and in particular are made of metal. In certain configurations, the rod elements and the pins have different diameters, such that the first and second receiving grooves are correspondingly dimensioned differently.

In certain configurations, the first and second clamping jaws have two second receiving grooves running parallel to each other, each for receiving a pin. To fix a fracture in place by means of the external fixator, typically a number of pins, most commonly two pins, is driven into each individual bone fragment, which pins are accordingly arranged relatively close together. By means of a single connecting apparatus, two pins can be connected to, for example, one rod element of the external fixator, such that the number of components required to stabilize the fracture is reduced. In addition, the difficulty of assembly is reduced, since the two pins inserted into the second receiving grooves are fixed in a non-positive and/or frictional manner by means of the tensile force applied in the axial direction; all the other degrees of freedom of the connecting apparatus—in particular, the orientation of the first and second clamping arrangements with regard to the rotary axis and the pivot axis and any rod element inserted into the first receiving grooves— are locked.

In certain configurations, the first and second clamping jaws are provided with interlocking structures which are designed to block relative rotation of the first and second clamping jaws. For example, one of the first or second clamping jaws has at least one pin protruding at the end face, which engages in a blind-hole-like depression that is made in the other of the first or second clamping jaws. This measure ensures that the first and/or second receiving grooves made in the first and second clamping jaws always run parallel.

In certain configurations, the traction means is movably guided at the end in a joint, in particular a ball joint, of the connecting apparatus, for example in such a way that the traction means is pivotable about two axes running perpendicular to each other. The traction means, which is, in particular, rigid, is thus movably mounted, such that the first and the second clamping arrangements can be adjusted relative to each other, in particular with respect to the pivot axis and the axis of rotation. For example, the joint is formed in a central region of the clamping jaw of the first or second clamping arrangement, which clamping jaw is located on the end with respect to the axial direction.

In certain configurations, the traction means is designed as a screw with a head end that is at least partially spherical in shape, with the head end being guided in a joint socket of the joint. In certain configurations, the joint socket is arranged, for example, in the middle or in a central region of a component of the connecting apparatus arranged on the end thereof. The joint socket with the head end guided therein forms a type of ball joint, such that the screw is pivotable substantially freely with respect to two axes which are perpendicular to each other and run through the joint.

In certain configurations in which the traction means is designed as a screw, the axial direction is predetermined by the orientation of the central longitudinal axis of the screw. In particular, the screw has an external thread, which is designed as a partial or full thread. An adjusting means, in particular a handwheel, a star knob, a screw or a screw nut, can be screwed onto the external thread to create the tensile load—or is screwed onto the external thread to create the tensile load.

In certain configurations, at least one groove is created in the head end of the traction means, into which groove a projection protruding past the joint socket, or a lug protruding past the joint socket, engages in such a way that rotation of the screw about the axial direction is at least restricted. This measure at least largely prevents the screw from rotating about its central longitudinal axis or about the axial direction, such that the adjusting means, in particular the handwheel, the star knob, the screw or the screw nut, can simply be screwed onto the thread of the screw to create the tensile force. In other words, the projection engaging in the groove forms a kind of torque support for the tightening torque acting about the central longitudinal axis, which is exerted in the axial direction to create the tensile force. The interaction between the projection and the groove does not limit, or only insignificantly limits, the above-described mobility of the screw with regard to pivoting about the axes running through the joint.

The invention also relates to an external fixator having at least one connecting apparatus, in particular having at least one of the connecting apparatuses already described above. The external fixator basically has a modular structure with a plurality of components that can be connected to each other. The number and design of the components, particularly with regard to their dimensions, may vary. From a medical point of view, depending on the type and severity of the fracture, a different number of rod elements, pins and/or connecting apparatuses can be provided in order to achieve sufficient stabilization of the fracture. In addition, rod elements with different axial lengths and/or pins with different diameters and/or axial lengths can be provided-designed, for example, for anchoring in the tibia (Latin: tibia), in the femur (lat.: femur), in the ulna (lat.: ulna), in the radius (lat.: radius), in the humerus (lat.: humerus), in the pelvis (lat.: pelvis) or in metacarpal bones (lat.: Ossa metacarpi). It goes without saying that this list is not exclusive.

The external fixator includes:
    at least two pins that are designed for anchoring, in particular by screwing, into bone tissue,
    at least one rod element, and at least one connecting apparatus, in particular at least one of the connecting apparatuses already described above, which is designed to mechanically connect at least one of the pins to the at least one rod element.

The external fixator includes, in certain configurations:
    at least four pins, preferably six or eight pins, which are designed for anchoring, in particular by screwing, into bone tissue,
    two rod elements, in particular of different axial lengths, and
    at least two, for example three or four, connecting apparatuses, in particular at least two, for example three or four of the connecting apparatuses already described above, which are designed to mechanically connect at least one of the pins to the at least one rod element.

It should be understood that the external fixator can have any number of connecting apparatuses, pins and/or rod elements. In advantageous configurations, however, the external fixator does not have any components or parts that are structurally different from the connecting apparatuses, pins and/or rod elements mentioned. The provision of as few differently designed components as possible greatly simplifies the handling and assembly of the external fixator, since possible sources of error, which result in particular from incorrect use of a specific component when assembling the external fixator, can be avoided.

In certain configurations, the external fixator is provided or designed to be used multiple times, for example. In other configurations, the external fixator is intended or designed for single use. In this case, possible wear and tear of surface structures that provide a positive connection between different components of the external fixator or between different components of the connecting apparatus is rather uncritical.

According to the invention, a device for ambulatory emergency care comprises at least the following components:
    an external fixator, in particular one of the external fixators described above, having
    at least two, for example four, pins which are designed for anchoring, in particular by screwing, into bone tissue,
    at least one rod element, and
    at least one connecting apparatus, in particular at least two, for example three connecting apparatuses, which are designed to mechanically connect at least one of the pins to the at least one rod element—in particular, at least one of the connecting apparatuses already described above. According to the invention, a motor-driven fastening device for driving the pins into the bone tissue is provided, which is designed for one-handed operation by a user. Alternatively, according to the invention, a manually driven or manually drivable fastening device is provided for driving the pins into the bone tissue.

In the installed state, the external fixator forms a frame which is at least for the most part outside the body of an injured person, and which is used for the temporary fixation of a bone fracture, typically an open bone fracture. In addition to the components of the external fixator, such as in particular pins, rod elements and connecting apparatuses, the device also has the motor-driven fastening device or the manually driven fastening device for driving the pins into the bone tissue, and optionally has further medical devices such as wound clamps, scalpels, and/or further medical accessories, in particular materials for dressings, for ambulatory emergency care. The device thus comprises a number of components, and is designed in particular to be used as part of civil protection activities or in military conflicts, in particular if it can be assumed that a large number of injured people will have to be treated as quickly as possible as part of emergency procedures. Such situations can arise, for example, in the case of terrorist attacks, or natural disasters such as earthquakes.

As a rule, two people are necessary to treat a single injured person, since, in the prior art, in particular for anchoring the pins in the bone tissue, conventional, in particular manual, drilling devices are used, which one person has to operate with both hands. Another person typically has to immobilize the person during the emergency response.

The fastening device for driving in the pins according to the invention is, on the one hand, motor-driven and, on the other hand, is designed for one-handed actuation or operation. As a result, the external fixator can be applied by only one first responder. Especially in the context of so-called disaster recovery scenarios, in which a large number of injured people, for example several dozen or even hundreds of seriously injured people, have to be treated outside a hospital, this implies a significant unburdening of resources—since, on average, twice the number of first responders per time unit can treat the same number of injured people.

The advantages of fastening devices that can be operated manually are, in particular, their low purchase price, their independence from electricity, and the fact that they are largely maintenance-free.

The device for ambulatory emergency care typically contains all medical components that are necessary to stabilize bone fragments by means of the external fixator. In certain configurations, the device for ambulatory emergency care can have additional medical components, such that other medical procedures can also be carried out using the device for ambulatory emergency care.

In certain configurations, the motor-driven fastening device is designed as an electric screwdriver with a T-shaped grip. The fastening device is, for example, designed ergonomically for one-handed actuation and operation.

In certain configurations, the manually drivable fastening device is designed as a crank. In particular, the crank has an offset axis such that a front and a rear crank portion are oriented along an axis of rotation of the crank and a central crank portion is spaced apart from the axis of rotation, wherein the crank is manually driven or is drivable by rotation of the central crank portion about the axis of rotation. The crank thus has a yoke shape.

In certain configurations, the fastening device has a receptacle for the non-positive fastening of one of the pins. The receptacle of the fastening device is designed, for example, in the manner of a chuck.

In certain configurations, the fastening device has an energy storage device, in particular a disposable battery or a rechargeable battery. The device is provided in certain configurations for single or multiple use.

In certain configurations, the device comprises at least two rod elements (also: rods, poles, pole elements), which optionally have different axial lengths. The at least one connecting apparatus is designed to mechanically connect the at least two rod elements to each other. By means of the connecting apparatus, not only can the pins be fastened to the rod elements, but also the rod elements can be fastened to each other. Such a configuration is particularly desirable in the treatment of more complex fractures, such as those requiring a joint-bridging configuration.

In certain configurations, at least two of the pins have different axial lengths and/or diameters. Pins with different diameters and/or axial lengths can be designed for different medical applications, for example. The various pins can be designed in particular for anchoring in the tibia (Latin: tibia), in the femur (lat.: femur), in the ulna (lat.: ulna), in the radius (lat.: radius), in the humerus (lat.: humerus), in the pelvis (lat.: pelvis) or in metacarpal bones (lat.: Ossa metacarpi).

In certain configurations, at least some of the components of the device are sealed in a plastic case. In this way, contamination or impurities in the components of the device can be counteracted.

In certain configurations, the components welded into the plastic case are sterilized or can be sterilized. At least those components that come into direct contact with human tissue when the device is used, such as in particular the pins and/or any scalpels, clamps or the like, are preferably packaged in a sterile manner. In particular, all components of the device are packaged in a sterile manner and are preferably sterilized and welded into the plastic case.

In certain configurations, the device has a textile base to provide an environment for the procedure. In particular, the textile base can be spread out on the ground in order to create an at least comparatively clean surgical environment on which the further emergency medical procedures, in particular for applying the external fixator, can be carried out. The textile base has suitable dimensions for this. In the packaged state, in certain configurations, the other components of the device, which are fastened, for example, to the plastic case already described or are welded into the plastic case already described, can be enclosed.

In certain configurations, the at least one connecting apparatus is designed to mechanically connect the at least two pins to at least one of the rod elements. Since the connecting apparatus is designed to fasten a plurality of pins to the rod element, the number of connecting apparatuses required for mounting the external fixator can be reduced. This advantageously reduces the manufacturing costs of the device and its overall weight.

In certain configurations, the at least one connecting apparatus is designed to mechanically connect the at least two pins in a parallel orientation to at least one of the rod elements. The pins fastened to the connecting apparatus can be used, for example, to immobilize a single bone fragment.

The mechanical connection of the pins to the rod elements, or of the rod elements to each other, is typically achieved at least by creating a frictional connection. In certain configurations, the mechanical connection takes place alternatively or additionally by creating a positive connection which is established by mutually complementary surface structures.

The at least one connecting apparatus of the external fixator or device is in particular at least one of the connecting apparatuses already described above.

The connecting apparatus for the purpose of connecting pins and/or rod elements of the external fixator comprises in certain configurations a first clamping arrangement for fastening at least one pin and/or rod element and a second clamping arrangement for fastening at least one pin and/or rod element. The first and second clamping arrangements are rotatable relative to each other, for example via a rotary joint, about an axis of rotation, and pivotable relative to each other via a pivot joint about a pivot axis running perpendicular to the axis of rotation. In preferred configurations, a traction means that can be loaded with tensile loads is passed through the first and second clamping arrangement, the rotary joint, and the pivot joint. The tension-loadable traction means is designed to fix the first and second clamping arrangement in place by imparting a tensile force (or: tensile stress, tensile load) in the axial direction along the traction means, and to lock them in different angular positions with respect to the axis of rotation and the pivot axis.

The traction means has, in particular, an elongated shape that extends in the axial direction and is, for example, designed as a single piece—or is at least designed to be rigid. The axial direction is specified in particular by the longitudinal extension of the traction means. Since the one-piece, or rigid, traction means is passed through both the first and the second clamping arrangement, and also the rotary joint and the pivot joint, all degrees of freedom of the connecting apparatus can be fixed by imparting a tensile force in the axial direction along the traction means. On the one hand, these degrees of freedom relate to the rotations of the clamping arrangements relative to each other about the pivot axis and about the axis of rotation. On the other hand, the rod elements and/or pins in the clamping arrangements are fastened in a non-positive manner by the provision of the tensile force in the axial direction along the traction means. For this purpose, the first clamping arrangement and the second clamping arrangement have, for example, first and second clamping jaws that can be braced against each other. To completely fix and lock the connecting apparatus, it is only necessary to provide a tensile stress acting along the traction means; this can be done, for example, by tightening a single adjusting means, such as an adjusting screw or a screw nut. The effort required to operate and apply an external fixator having such connecting apparatuses is therefore reduced. In addition, the functionality of the external fixator is particularly easy to grasp intuitively, such that it can also be applied by a person who has not been medically trained or is at least comparatively inexperienced, in particular as part of an emergency medical procedure.

In certain configurations, the traction means is designed, for example, as a screw. In such embodiments, the axial direction corresponds to the direction in which the longitudinal center axis of the screw is oriented. In general, the axial direction differs from the direction of the pivot axis because the orientation of the axis of rotation depends on the angular position of the clamping arrangements about the pivot axis. In a starting position, in which the clamping arrangements are not displaced relative to each other with respect to the pivot axis, the axis of rotation runs coaxially with the axial direction, which is substantially defined by the longitudinal extension of the traction means.

In certain configurations, the rotary joint comprises at least two adjacent rotary joint components which are mounted such that they can rotate relative to each other about the axis of rotation, and which can be locked in different angular positions relative to each other by means of the traction means. A first spring means is arranged between the rotary joint components, and is designed to brace the rotary joint components away from each other in the axial direction. The traction means is guided, for example, centrally through the rotary joint components that form the rotary joint. The first spring means produces a spring force acting in the axial direction, which spring force is designed to drive the rotary joint components apart, such that they can be moved with respect to each other into the desired angular position, in particular by hand, in the unloaded state in which the traction means is not or is only slightly under tensile load. By creating the tensile force in the axial direction along the traction means, the rotary joint components can then be locked in the desired angular position—that is, the tensile load acting to lock the connecting apparatus is oriented against the spring force created by the first spring means.

In certain configurations, the first spring means is designed, for example, in the form of a wave spring. In certain configurations, the first spring means can, for example, have rings or ring elements arranged concentrically to each other and around the axial axis A, which are connected to each other via axially running webs. The first spring means is preferably designed to absorb forces occurring in the axial direction and transversely, which forces act on the rotary joint or on the rotary joint components, for example, in directions that deviate from the direction in which the axis of rotation is oriented. For this purpose, in certain configurations, the first spring means is designed as a cylinder beam spring that can withstand bending loads or is subjected to bending loads. The first spring means can be made of titanium or aluminum, for example, or can comprise titanium or aluminum.

The first spring means can be designed as a separate component of the connecting apparatus. In advantageous configurations, the first spring means is formed as a single piece with one of the rotary joint components. In certain configurations, the first spring means can have a ring element, for example, which is connected to one of the rotary joint components via webs. Furthermore, the spring element is preferably designed to additionally guide and center the two rotary joint components. For this purpose, the spring means projects, in particular in the axial direction A, beyond the rotary joint component, or protrudes at least partially from it in the axial direction A.

In certain configurations, the adjacent rotary joint components, together with the traction means which is guided centrally through the rotary joint components, for example, implement the functionality of the pivot joint, i.e., the rotation of the first and second clamping arrangements relative to each other and about the axis of rotation. In certain configurations in which the traction means is guided centrally through the rotary joint components, these can be rotated relative to each other and about the traction means, preferably through an angular range of 360°.

In certain configurations, the rotary joint components are, for example, substantially disk-shaped and arranged opposite each other on the end faces.

In certain configurations, the first clamping arrangement is connected to one of the rotary joint components and the second clamping arrangement is connected to the other rotary joint component in a rotationally fixed manner, at least with respect to a rotation about the axis of rotation. In certain configurations, at least one of the rotary joint components is implemented as an integral part of the first or second clamping arrangement. For example, at least one of the rotary joint components forms a (first or second) clamping jaw of the first or second clamping arrangement. In other words, in certain configurations, at least one of the rotary joint components can be formed as a single piece together with a (first or second) clamping jaw of the first and/or second clamping arrangement, for example. In this way, the number of components required to form the connecting apparatus can be reduced, and weight can thus be saved in particular. This is particularly advantageous when the external fixator presented here is used in the field of civil protection and/or the military, since it may be necessary in such cases to carry the external fixator as part of emergency medical equipment in the field, especially over longer distances.

In certain configurations, the rotary joint components have first surface structures which are arranged opposite each other and are designed to be complementary to each other, designed to engage in each other with a positive connection in different angular positions. Correspondingly, the rotational degree of freedom of the connecting apparatus is locked in relation to the movement of the clamping arrangements about the axis of rotation with the additional aid of a positive connection. In this way, the force required to lock this degree of freedom can be significantly reduced compared to designs that are based exclusively on a non-positive and/or frictional locking, and the mechanical stability of the mounted external fixator can be improved. In particular, it can be achieved that the tensile load required for adequately fixing the components connected by means of the connecting apparatus can be created by a person without tools and/or manually, for example by tightening a single adjusting means that is in an operative connection with the traction means. This adjusting means is, for example, a hand wheel, a star knob, a screw or a screw nut which is in an operative connection with the traction means to create the tensile load.

In certain configurations, the first surface structure has, for example, a toothed or corrugated structure, at least in regions thereof. In certain configurations, the first surface structures are designed, for example, as circumferential crown teeth that protrude axially in the direction of the axis of rotation, and which are arranged opposite each other and are designed as spur gear teeth to engage in each other with a positive connection.

In certain configurations, the pivot joint comprises at least two adjoining pivot joint components which are mounted such that they can pivot relative to each other about the pivot axis, and which can be locked in different angular positions relative to each other by means of the traction means. A second spring means is arranged between the pivot joint components, and is designed to brace the pivot joint components away from each other in the axial direction. The traction means is guided, for example, centrally through the pivot joint components that form the pivot joint. The second spring means produces a spring force acting in the axial direction, which spring force is designed to drive the pivot joint components apart, such that they can be moved with respect to each other into the desired angular position, in particular by hand, in the unloaded state in which the traction means is not or is only slightly under tensile load. By creating the tensile force in the axial direction along the traction means, the pivot joint components can then be locked in the desired angular position—that is, the tensile load acting to lock the connecting apparatus is oriented against the spring force created by the second spring means.

In certain configurations, the second spring means is designed as a leaf spring, for example. In certain configurations, the leaf spring has a centrally arranged opening through which the traction means is guided.

Together with the traction means which is guided centrally through the pivot joint component, the mutually adjacent pivot joint components substantially implement the functionality of the pivot joint, i.e., the rotation of the first and second clamping arrangements relative to each other and about the pivot axis. In certain configurations, the pivot joint components are pivotable relative to each other through a limited angular range of less than 180°, in particular through an angular range of less than 90°. In certain configurations, the pivot joint components and/or the first clamping arrangement are/is pivotable relative to the second clamping arrangement through an angular range of at least 40°, for example in an angular range of approximately +/−20°, relative to a starting position.

In certain configurations, at least one of the pivot joint components has a central elongated hole through which the traction means is guided. The elongated hole forms a kind of slotted link along which the centrally guided traction means can be moved, such that the two clamping arrangements can be moved relative to each other about the pivot axis over a correspondingly large angular range.

The pivot joint components are, for example, substantially disk-shaped, and are arranged opposite each other. The oppositely arranged sides of the pivot joint components have, for example, at least partially curved portions which restrict the movement of the two pivot joint components relative to each other substantially to a pivot movement perpendicular to the axis of rotation. The mutually facing sides of the pivot joint components are shaped, for example, in such a way that the pivot joint components cannot be moved relative to each other about the axis of rotation. In other words, the pivot joint components in such configurations form, together with the traction means, a pivot joint which connects the first clamping arrangement to the second clamping arrangement in a rotationally fixed manner with regard to rotations about the axis of rotation.

In certain configurations, the first clamping arrangement is connected in a rotationally fixed manner to one of the pivot joint components, and the second clamping arrangement is connected in a rotationally fixed manner to the other pivot joint component—at least with respect to rotation about the pivot axis. In certain configurations, at least one of the pivot joint components is implemented as an integral part of the first or second clamping arrangement. For example, at least one of the pivot joint components forms a (first or second) clamping jaw of the first or second clamping arrangement. In other words, it is provided in certain configurations, for example, for at least one of the pivot joint components to be designed as a single piece together with a (first or second) clamping jaw of the first or second clamping arrangement. In this way, too, the number of components required to form the connecting apparatus can be reduced, and accordingly, in particular, weight and/or material costs can be saved.

In certain configurations it is provided that the function of one of the pivot joint components and the function of one of the rotary joint components is realized by a single component. Accordingly, this component acts both as a rotary and as a pivot joint component in order to further reduce the number of components required to implement the connecting apparatus. The rotary joint and the pivot joint are formed, in certain configurations, for example, by only three components, which are substantially disk-shaped and which adjoin each other in succession in the axial direction, and provide a connection between the first and the second clamping arrangement in such a way that they can be positioned in different angular positions relative to each other, both with regard to the pivot axis and to the axis of rotation. In certain configurations in which (first or second) clamping jaws of the first and/or the second clamping arrangement also function as rotary joint or pivot joint components, the number of components is reduced even further. In this way, the installation space required to implement the connecting apparatus is reduced in the axial direction and additional weight is saved.

In certain configurations, the pivot joint components have second surface structures which are arranged opposite each other and are designed to be complementary to each other, and are designed to engage in each other with a positive connection in different angular positions. Correspondingly, the rotational degree of freedom of the connecting apparatus is locked in relation to the movement of the first and second clamping arrangements about the pivot axis with the additional aid of a positive connection. In this way, the force required to lock this degree of freedom can be significantly reduced compared to designs that are based exclusively on a non-positive and/or frictional locking, and the mechanical stability of the mounted external fixator can be improved. The tensile load required for adequately fixing the components connected by means of the connecting apparatus can be created by a person without tools and/or manually, for example by tightening a single adjusting means that is in an operative connection with the traction means. This adjusting means is, for example, a hand wheel, a star knob, a screw or a screw nut which is in an operative connection with the traction means to create the tensile load.

In certain configurations, the second surface structures have, for example, toothed or corrugated structures, at least in regions. In certain configurations, the second surface structures include, for example, a plurality of grooves, flutings, and/or ridge-like ribs running parallel to the pivot axis. In certain configurations, the ridge-like ribs are designed, for example, to be complementary to the grooves or flutings. In order to provide the positive connection, the ridge-like ribs of one pivot joint component are arranged opposite the grooves or flutings of the other pivot joint component, such that they can engage in each other in the manner of spur gear teeth.

In certain configurations, the first clamping arrangement and/or the second clamping arrangement has/have two opposite first and second clamping jaws that can be braced against each other by means of the tensile force acting in the axial direction, and which each have oppositely arranged first receiving grooves for receiving a rod element. The rod elements (also: rods, posts) of the external fixator can be inserted into the receiving grooves and connected in different spatial configurations by means of the connecting apparatus already described, and can be locked in a non-positive and/or frictional manner by the application of the axial tensile load.

In certain configurations, the first receiving grooves are provided, at least in portions thereof, with third surface structures which are designed to positively engage in complementary surface structures of a rod element. In certain configurations, the third surface structure comprises, for example, a plurality of grooves, flutings, and/or ridge-like ribs running parallel to each other. In such designs, the rod elements are thus fixed with the additional aid of a positive connection, as a result of which significantly greater torsional moments can be transmitted between the connecting apparatus and the rod elements compared to a pure non-positive and/or frictional connection.

In certain configurations, the first clamping arrangement and/or the second clamping arrangement has/have two opposite first and second clamping jaws that can be braced against each other by means of the tensile force acting in the axial direction, and which each have oppositely arranged second receiving grooves for receiving a pin. The pin can be inserted into the receiving grooves of the opposite first and second clamping jaws and locked in a non-positive and/or frictional manner by the application of the axial tensile load. The pin is designed to be driven into the bone tissue of an injured person or a patient, and has a tap thread for this purpose, for example. Typically, the pin is firmly connected to the connecting apparatus after it has been anchored in the bone tissue. In certain configurations, the pins are designed as threaded rods, and in particular are made of metal. In certain configurations, the rod elements and the pins have different diameters, such that the first and second receiving grooves are correspondingly dimensioned differently.

In certain configurations, the first and second clamping jaws have two second receiving grooves running parallel to each other, each for receiving a pin. To fix a fracture in place by means of the external fixator, typically a number of pins, most commonly two pins, is driven into each individual bone fragment, which pins are accordingly arranged relatively close together. By means of a single connecting apparatus, two pins can be connected to, for example, one rod element of the external fixator, such that the number of components required to stabilize the fracture is reduced. In addition, the difficulty of assembly is reduced, since the two pins inserted into the second receiving grooves are fixed in a non-positive and/or frictional manner by means of the tensile force applied in the axial direction; all the other degrees of freedom of the connecting apparatus—in particular, the orientation of the first and second clamping arrangements with regard to the rotary axis and the pivot axis and any rod element inserted into the first receiving grooves—are locked.

In certain configurations, the first and second clamping jaws are provided with interlocking structures which are designed to block relative rotation of the first and second clamping jaws. For example, one of the first or second clamping jaws has at least one pin protruding at the end face, which engages in a blind-hole-like depression that is made in the other of the first or second clamping jaws. This measure ensures that the first and/or second receiving grooves made in the first and second clamping jaws always run parallel.

In certain configurations, the traction means is movably guided at the end in a joint, in particular a ball joint, of the connecting apparatus, for example in such a way that the traction means is pivotable about two axes running perpendicular to each other. The traction means, which is, in particular, rigid, is thus movably mounted, such that the first and the second clamping arrangements can be adjusted relative to each other, in particular with respect to the pivot axis and the axis of rotation. For example, the joint is formed in a central region of the clamping jaw of the first or second clamping arrangement, which clamping jaw is located on the end with respect to the axial direction.

In certain configurations, the traction means is designed as a screw with a head end that is at least partially spherical in shape, with the head end being guided in a joint socket of the joint. In certain configurations, the joint socket is arranged, for example, in the middle or in a central region of a component of the connecting apparatus arranged on the end thereof. The joint socket with the head end guided therein forms a type of ball joint, such that the screw is pivotable substantially freely with respect to two axes which are perpendicular to each other and run through the joint.

In certain configurations in which the traction means is designed as a screw, the axial direction is predetermined by the orientation of the central longitudinal axis of the screw. In particular, the screw has an external thread, which is designed as a partial or full thread. An adjusting means, in particular a handwheel, a star knob, a screw or a screw nut, can be screwed onto the external thread to create the tensile load—or is screwed onto the external thread to create the tensile load.

In certain configurations, at least one groove is created in the head end of the traction means, into which groove a projection protruding past the joint socket, or a lug protruding past the joint socket, engages in such a way that rotation of the screw about the axial direction is at least restricted.

This measure at least largely prevents the screw from rotating about its central longitudinal axis or about the axial direction, such that the adjusting means, in particular the handwheel, the star knob, the screw or the screw nut, can simply be screwed onto the thread of the screw to create the tensile force. In other words, the projection engaging in the groove forms a kind of torque support for the tightening torque acting about the central longitudinal axis, which is exerted in the axial direction to create the tensile force. The interaction between the projection and the groove does not limit, or only insignificantly limits, the above-described mobility of the screw with regard to pivoting about the axes running through the joint.

The external fixator of the device is in particular one of the external fixators already described above.

In certain configurations, the external fixator has at least one connecting apparatus which is designed as already described above. The external fixator basically has a modular structure with a plurality of components that can be connected to each other. The number and design of the components, particularly with regard to their dimensions, may vary. From a medical point of view, depending on the type and severity of the fracture, a different number of rod elements, pins and/or connecting apparatuses can be provided in order to achieve sufficient stabilization of the fracture. In addition, rod elements with different axial lengths and/or pins with different diameters and/or axial lengths can be provided-designed, for example, for anchoring in the tibia (Latin: tibia), in the femur (lat.: femur), in the ulna (lat.: ulna), in the radius (lat.: radius), in the humerus (lat.: humerus), in the pelvis (lat.: pelvis) or in metacarpal bones (lat.: Ossa metacarpi). It goes without saying that this list is not exclusive.

The external fixator includes:

at least two pins that are designed for anchoring, in particular by screwing, into bone tissue, at least one rod element, and at least one connecting apparatus, in particular one of the connecting apparatuses already described above, which is designed to mechanically connect at least one of the pins to the at least one rod element.

The external fixator includes, in certain configurations:

at least four pins, preferably six or eight pins, which are designed for anchoring, in particular by screwing, into bone tissue, two rod elements, in particular of different axial lengths, and at least two, for example three or four, connecting apparatuses, in particular at least two, for example three or four of the connecting apparatuses already described above, which are designed to mechanically connect at least one of the pins to the at least one rod element.

It should be understood that the external fixator can have any number of connecting apparatuses, pins and/or rod elements. In advantageous configurations, however, the external fixator does not have any components or parts that are structurally different from the connecting apparatuses, pins and/or rod elements mentioned. The provision of as few differently designed components as possible greatly simplifies the handling and assembly of the external fixator, since possible sources of error, which result in particular from incorrect use of a specific component when assembling the external fixator, can be avoided.

In certain configurations, the external fixator is provided or designed to be used multiple times, for example. In other configurations, the external fixator is intended or designed for single use. In this case, possible wear and tear of surface structures that provide a positive connection between different components of the external fixator or between different components of the connecting apparatus is rather uncritical.

In a method for carrying out a medical procedure in ambulatory emergency care, at least some of the pins are driven into bone fragments of an injured person or a patient using the fastening device designed for one-handed operation by a user. This is preferably done using the motor-driven fastening device already described, which in embodiments is designed with a T-shaped grip for better handling. Alternatively, this is done using the previously described, manually drivable fastening device, which in certain configurations is designed with a knob as a grip for better handling.

If necessary, access to the bone fragments, for example in the form of a channel which is cut into the surrounding muscle tissue of the injured person, is created before the pins are driven in, in particular using a suitable cutting tool. A sleeve (also: tissue protection sleeve) is preferably inserted into the access created in this way in order to protect the surrounding muscle tissue when the pins are being driven in or screwed in. After the pins have been driven into the respective bone parts to be fixed, the sleeves are typically removed and the external fixator is assemble—i.e., the pins are connected to each other via connecting apparatuses and a rod element or several rod elements in such a way that at least the point of the fracture is bridged by the external fixator. This is generally done to make the injured person fit to be transported, so that they can then be taken to a hospital or infirmary for further treatment.

For a further description of the invention, reference is made to the embodiments shown in the drawings, wherein—in schematic illustrations:

BRIEF DESCRIPTION OF THE DRAWINGS

Corresponding parts and components are each provided with the same reference signs in all figures.

DETAILED DESCRIPTION

Figure 21:
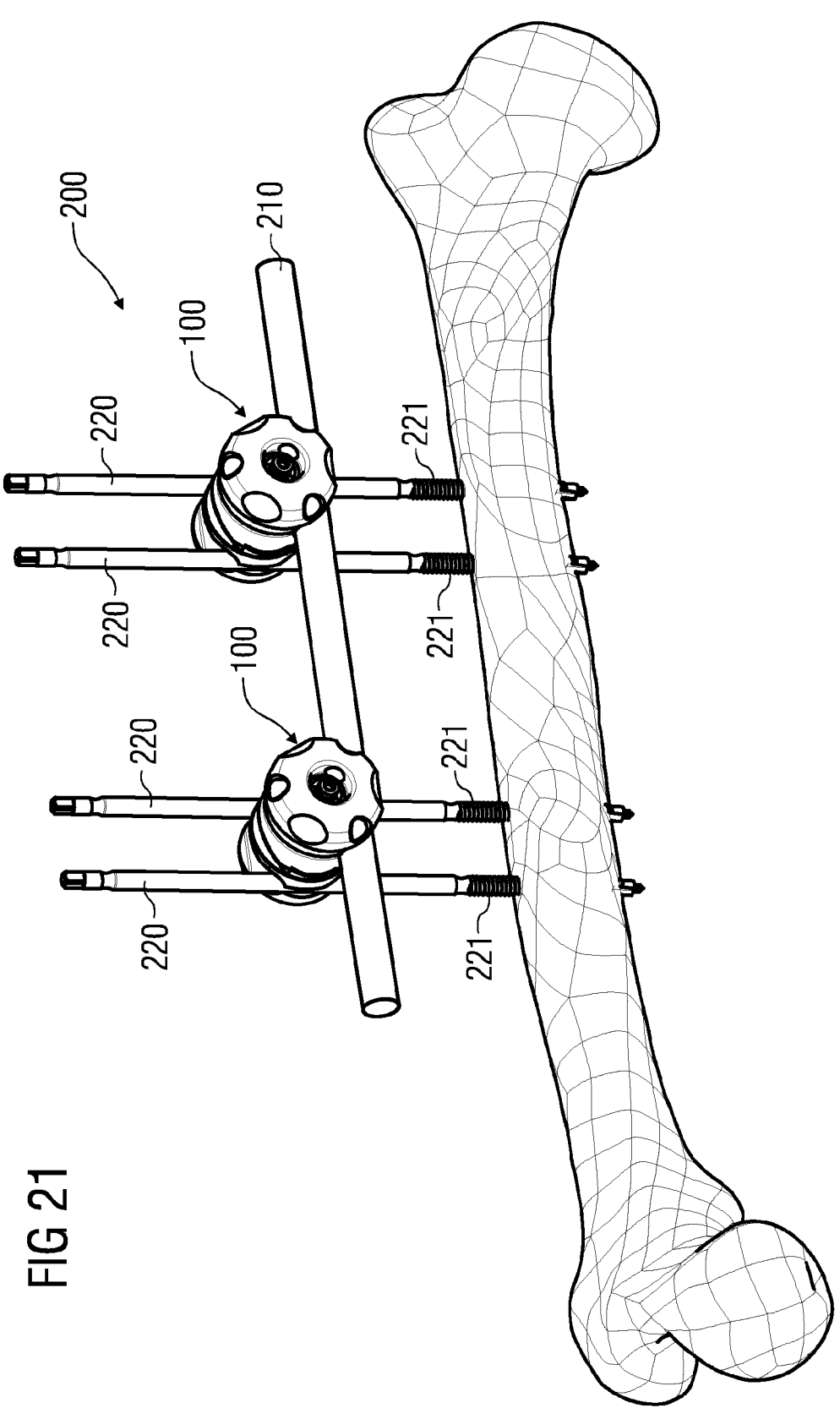
FIG. 21 shows the external fixator in a possible example of a configuration for fixation of a femoral fracture.

FIGS. 1 through 7 show a connecting apparatus 100 of an external fixator 200, which is illustrated in an exemplary configuration in FIG. 21.

FIGS. 8 to 20 show details of various components of the connecting apparatus 100.

The external fixator 200 includes, as shown for example in FIG. 21, in addition to the connecting apparatuses 100, at least one rod-shaped rod element 210 and a plurality of pins 220, which are designed as threaded rods for the purpose of being anchored in human or animal bone tissue, and which have tap threads 211 at each end for this purpose.

The connecting apparatus 100 is designed to connect pins 220 and/or rod elements 210 to each other in a non-positive manner, optionally with the additional aid of a positive connection. For this purpose, the connecting apparatus 100 has first and second clamping arrangements 20, 30, each with oppositely arranged first and second clamping jaws 21, 22, 31, 32, between which pins 220 and/or rod elements 210 can be clamped by means of a force acting in the axial direction A.

Figure 1:
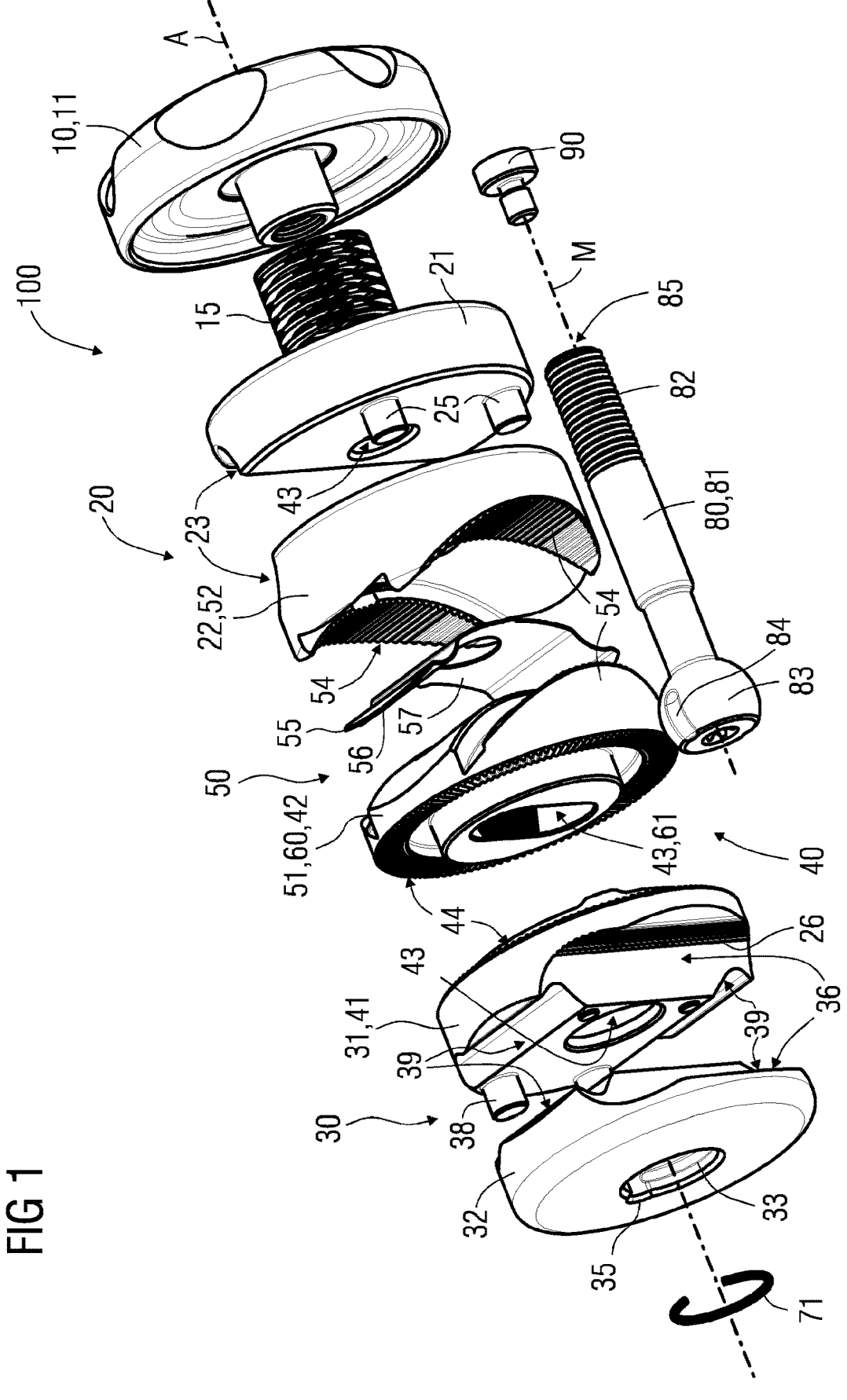
FIG. 1 shows a possible embodiment of a connecting apparatus of an external fixator in an exploded view.

As shown in particular in FIG. 1, the connecting apparatus 100 has an axial construction, with a plurality of approximately disk-shaped components which, at least in a starting position, are arranged opposite each other on the ends. In particular, the above-mentioned first and second clamping jaws 21, 22, 31, 32 of the first and second clamping arrangement 20, 30, and a joint component 60 situated between the second clamping jaw 22 of the first clamping arrangement 20 and the first clamping jaw 31 of the second clamping arrangement 30, are approximately disk-shaped, and can be arranged, or are arranged, on end faces opposite each other. A traction means 80 is passed centrally through the first and second clamping jaws 21, 22, 31, 32 of the first and second clamping arrangements 20, 30 and the joint component 60. The traction means 80 is made as a single piece or as a single part, and is rigid.

In the embodiment shown, which is not to be interpreted as limiting, the traction means is designed as a screw 81 with an external thread 82 and a head end 83 of approximately spherical design. Two diametrically opposite grooves 84 are introduced in the head end 83. The head end 83 of the screw 82 is movably guided in a joint socket 33 which is created in a central region of the second clamping jaw 32 of the second clamping arrangement 30. The at least partially spherical head end 83 of the screw 81 forms a joint 70 together with the joint socket 33, in particular in the manner of a ball joint, which allows pivoting movements of the screw 81 relative to the second clamping jaw 32 of the second clamping arrangement 30. The joint socket 33 has two diametrically opposed projections 34 or lugs which are shown in detail in FIG. 8. In the final assembled state of the connecting apparatus 100, the projections 34 engage in the grooves 84 and thus prevent a rotation of the screw 81 about its central longitudinal axis M, or at least limit such a rotation. The orientation of the central longitudinal axis M corresponds to the axial direction A in the final assembled state of the connecting apparatus 100 (see in particular FIGS. 2 to 7). A further groove 35 is created in the region of the joint socket 33 (see in particular FIG. 1 or 8), which is provided for receiving a retaining ring 71. The retaining ring 71 is designed to prevent the screw 81 from being displaced in the axial direction A, in particular when the connecting apparatus 100 is being assembled.

At the end of the screw 81 which is arranged opposite the head end 83, there is an internal thread 85 into which a retaining screw 90 is screwed. In the final assembled state of the connecting apparatus 100, the retaining screw 90 is used to secure an adjusting means 10, which is designed in the form of a hand wheel 11 in the illustrated embodiment, which is not to be interpreted as being restrictive. The hand wheel 11 is screwed onto the external thread 82 of the screw 81. The retaining screw 90 limits the axial range of motion of the handwheel 11, in particular in such a way that the handwheel 11 cannot be unscrewed from the external thread 82 by a simple turning movement in the final assembled state.

The adjusting means 10 is used to create a tensile load or tensile force acting in the axial direction A. By exerting the tensile force in the axial direction A, rod elements 220 and/or pins 210 arranged between the clamping jaws 21, 22, 31, 32 can be fixed at least in a non-positive and/or frictional manner. The first and second clamping jaws 21, 22 of the first clamping arrangement 20 have opposite first receiving grooves 23 running parallel to each other. The first and second clamping jaws 31, 32 of the second clamping arrangement 30 also have opposite first receiving grooves 36 running parallel to each other. The first receiving grooves 23, 36 are used to hold rod elements 220 and are dimensioned accordingly. Inserted rod elements 220 can be fixed in the region of the first receiving grooves 23, 36 by the application of the axial tensile load.

The first and second clamping jaws 21, 22, 31, 32 of the first and second clamping arrangements 20, 30 are provided with interlocking structures designed to restrict rotation of the first clamping jaw 21 relative to the second clamping jaw 22 of the first clamping arrangement 20, and/or rotation of the first clamping jaw 31 relative to the second clamping jaw 32 of the second clamping arrangement 30.

In the illustrated embodiment, which is not to be interpreted as limiting, these interlocking structures are designed as blind-hole-like depressions 24, 37 and pins 25, 38.

Figure 16:
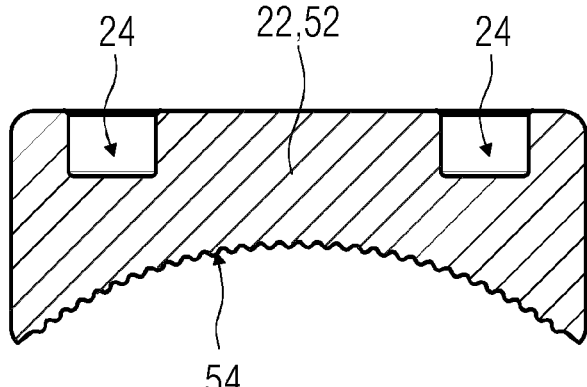
FIG. 16 shows details of a further clamping jaw of the connecting apparatus of FIG. 1 in a sectional view.
Figure 17:
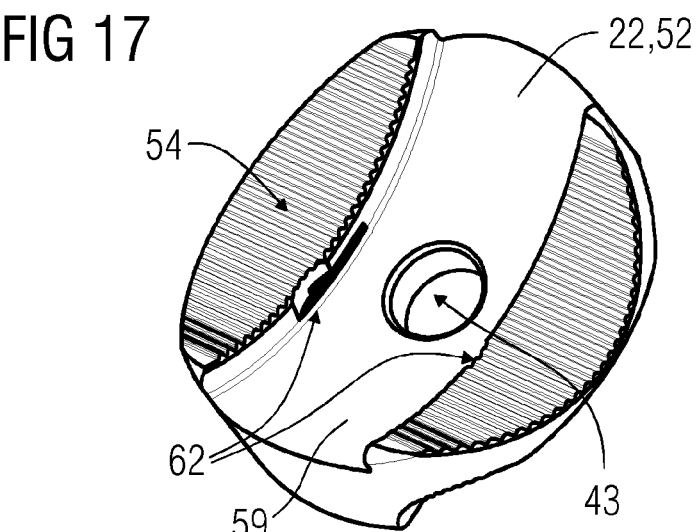
FIG. 17 shows the clamping jaw of FIG. 16 in a perspective view.

FIG. 16 shows further details of the second clamping jaw 22 of the first clamping arrangement 20 in a sectional view. The blind hole-like depressions 24 are introduced into the side of the second clamping jaw 22 which is arranged opposite the first clamping jaw 21 of the first clamping arrangement 20. As shown in particular in FIG. 1, the pins 25 protrude from the face of the first clamping jaw 21 and engage in the blind hole-like depressions 24 in the final assembled state (see in particular FIGS. 2 to 7).

Figure 9:
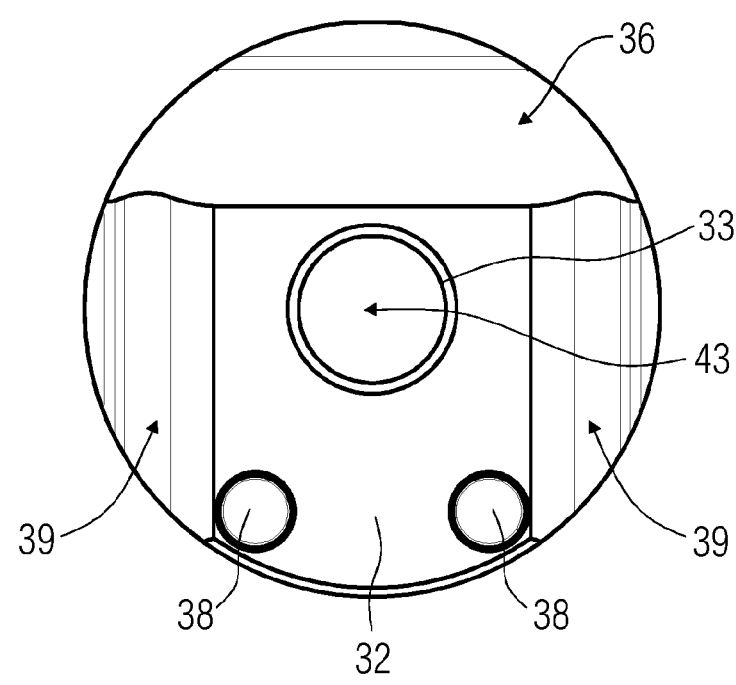
FIG. 9 shows the clamping jaw of FIG. 8 in a plan view.
Figure 10:
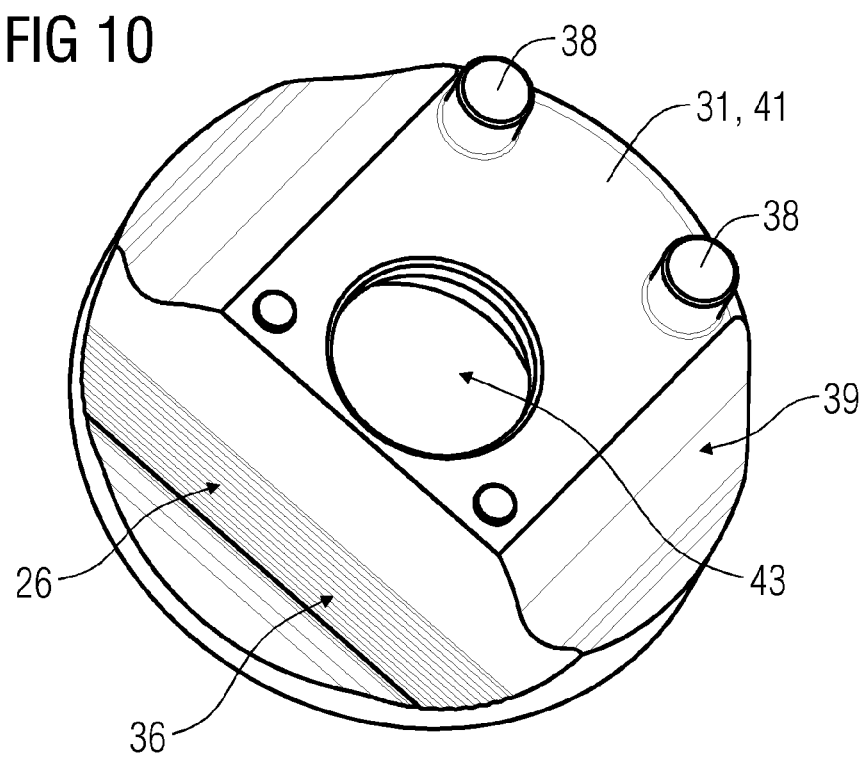
FIG. 10 shows a further clamping jaw of the connecting apparatus of FIG. 1 in detail in a perspective view.
Figure 11:
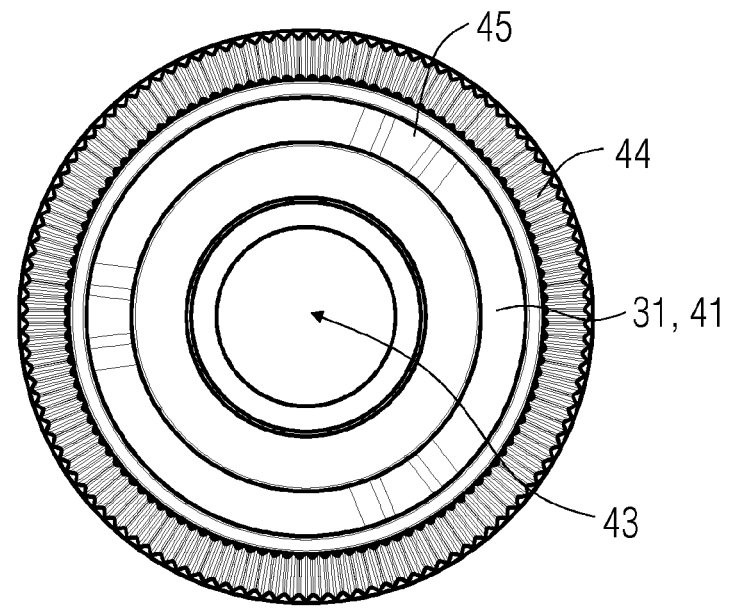
FIG. 11 shows the clamping jaw of FIG. 10 in a plan view.

Correspondingly, blind-hole-like depressions 38, as shown in particular in FIG. 9, are created in the second clamping jaw 32 of the second clamping arrangement 30. The pins 38 protrude from the end face of the first clamping jaw 31 of the second clamping arrangement 30, and engage in the blind hole-like depressions 37 in the final assembled state (see, for example, FIGS. 2 to 7).

In other configurations, the interlocking structures are inverted, i.e., the pins 25, 38 can be provided on the second clamping jaws 22, 32 and the blind hole-like depressions 24, 37 can be provided on the first clamping jaws 21, 31 of the first and/or second clamping arrangement 20, 30.

In the illustrated embodiment, which is not to be interpreted as being restrictive, the first receiving grooves 23, 36 are provided in some portions with third surface structures 26 (see, for example, FIG. 1 or FIG. 10), which are designed to positively engage in complementary surface structures 212 of a rod element 210. The third surface structure 26 comprises a plurality of grooves and ribs which run parallel to each other and which extend along the receiving grooves 23, 36. The rod elements 210 are thus fixed with the additional aid of a positive connection.

In the embodiment shown, which is not to be interpreted as limiting, the second clamping arrangement 30 has, in addition to the first receiving grooves 36, second receiving grooves 39 (see in particular FIG. 9 or 10), which are designed to receive pins 210 and are dimensioned somewhat smaller for this purpose, for example. Upon application of the axial tensile load, the inserted pins 210 can be fixed in the region of the second receiving grooves 31.

In the illustrated and non-limiting embodiment, two second receiving grooves 39 are made in the first clamping jaw 31 of the second clamping arrangement 30, and two second receiving grooves 39 are made in the second clamping jaw 32 of the second clamping arrangement 30. The second receiving grooves 39 made in the first clamping jaw 31 are arranged opposite the receiving grooves 39 made in the second clamping jaw 32. The second receiving grooves 39 run parallel to each other, such that in the second clamping arrangement 30, two pins 210 can be non-positively and frictionally fixed in a parallel orientation to each other. In the embodiment shown, the second receiving grooves 39 are oriented perpendicularly to the first receiving grooves 36 of the second clamping arrangement 30, but deviations from this are possible and provided in alternative configurations.

Figure 20:
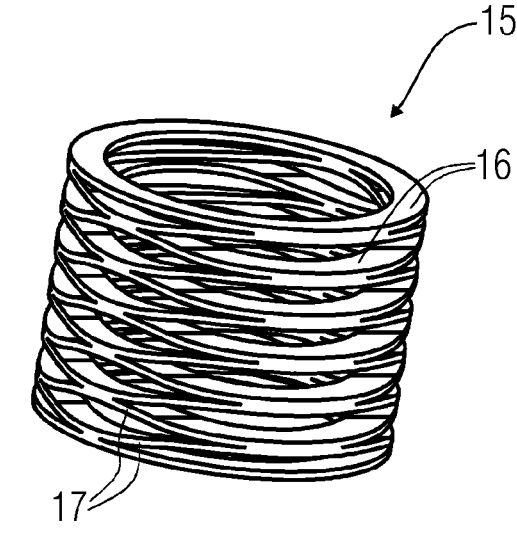
FIG. 20 shows a spring means designed as a wave spring of the connecting apparatus of FIG. 1 in a perspective view.

A spring 15 is arranged between the adjusting means 10 and the first clamping jaw 21 of the first clamping arrangement 20, which is designed, for example, as a helical or compression spring, as shown in particular in FIG. 1, or as a wave spring, as shown in particular in FIG. 20. The spring 15 ensures a certain mobility of the first and second clamping jaws 21, 22, 31, 32 of the first and second clamping arrangements 20, 30 when the traction means is not, or is only slightly, under tensile load. This enables a certain mobility of the clamping jaws 21, 22, 31, 33 with a low axial load in such a way that, for example, the pins 220 and/or the rod elements 210 can simply be clipped in the lateral direction into the corresponding first and/or second receiving grooves 23, 36, 39. The receptacles formed by the first and/or second receiving grooves 23, 36, 39 thus form a kind of snap-in connection which can be locked by means of the tensile load acting along the traction means 80.

The variant embodiment of the spring 15 shown in FIG. 20 has a substantially cylindrical shape, and is advantageously designed to absorb transverse loads acting in a direction deviating from the axial direction A. The spring 15 designed as a wave spring comprises a plurality of ring elements 16, which are connected to each other via webs 17 which are designed to be flexible at least in sections.

The first clamping arrangement 20 and the second clamping arrangement 30 can be rotated relative to each other about an axis of rotation D via a rotary joint 40 and pivoted relative to each other about a pivot axis S via a pivot joint 50. In the embodiment illustrated in the drawing, which is not to be interpreted as limiting, the first clamping arrangement 20 and the second clamping arrangement 30 can be moved relative to each other about the axis of rotation D through the full angular range of 360°. With respect to the pivot axis S, the first clamping arrangement 20 and the second clamping arrangement 30 can be moved relative to each other through a limited angular range of approximately 40° (see in particular FIGS. 2 and 4).

Figure 4:
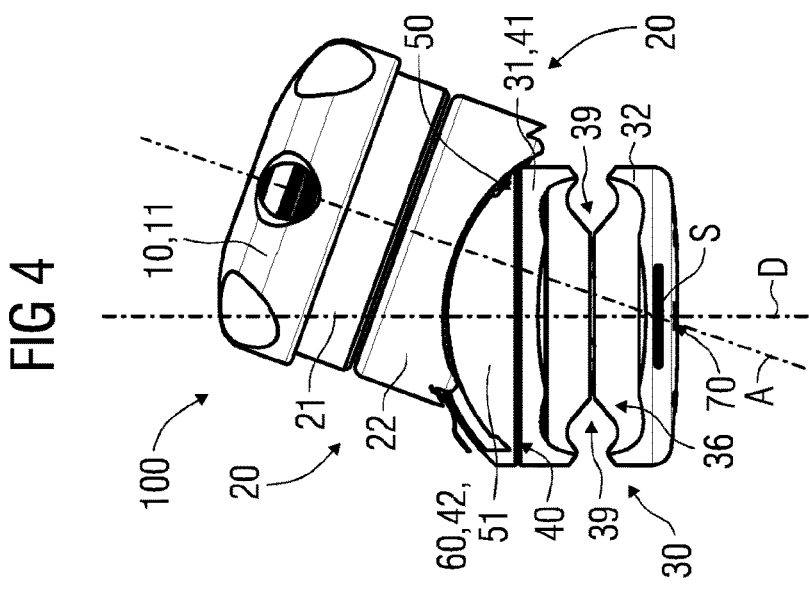
FIG. 4 shows the connecting apparatus of FIG. 1 in a further possible spatial configuration, from the side.
Figure 3:
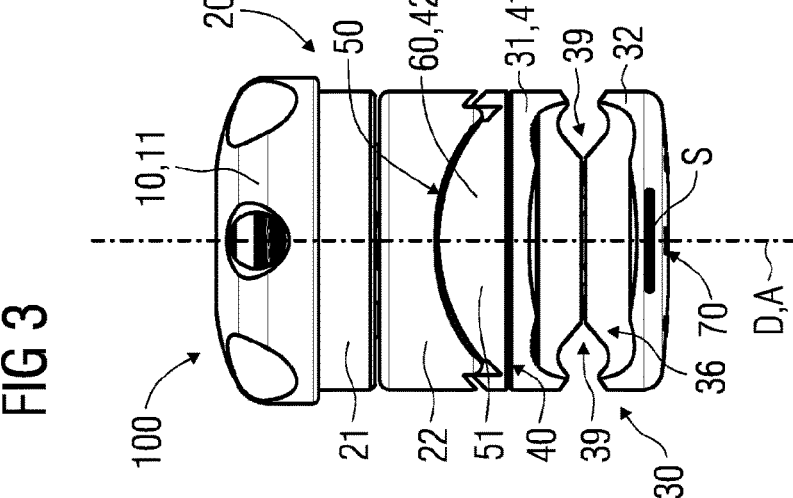
FIG. 3 shows the connecting apparatus of FIG. 1 in a further possible spatial configuration, from the side.
Figure 2:
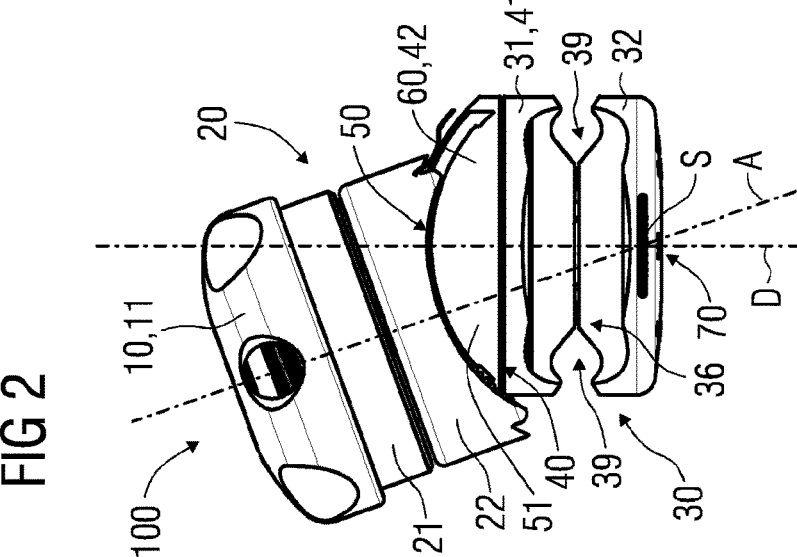
FIG. 2 shows the connecting apparatus of FIG. 1 in one possible spatial configuration, from the side.
Figures 5, 6, 7:
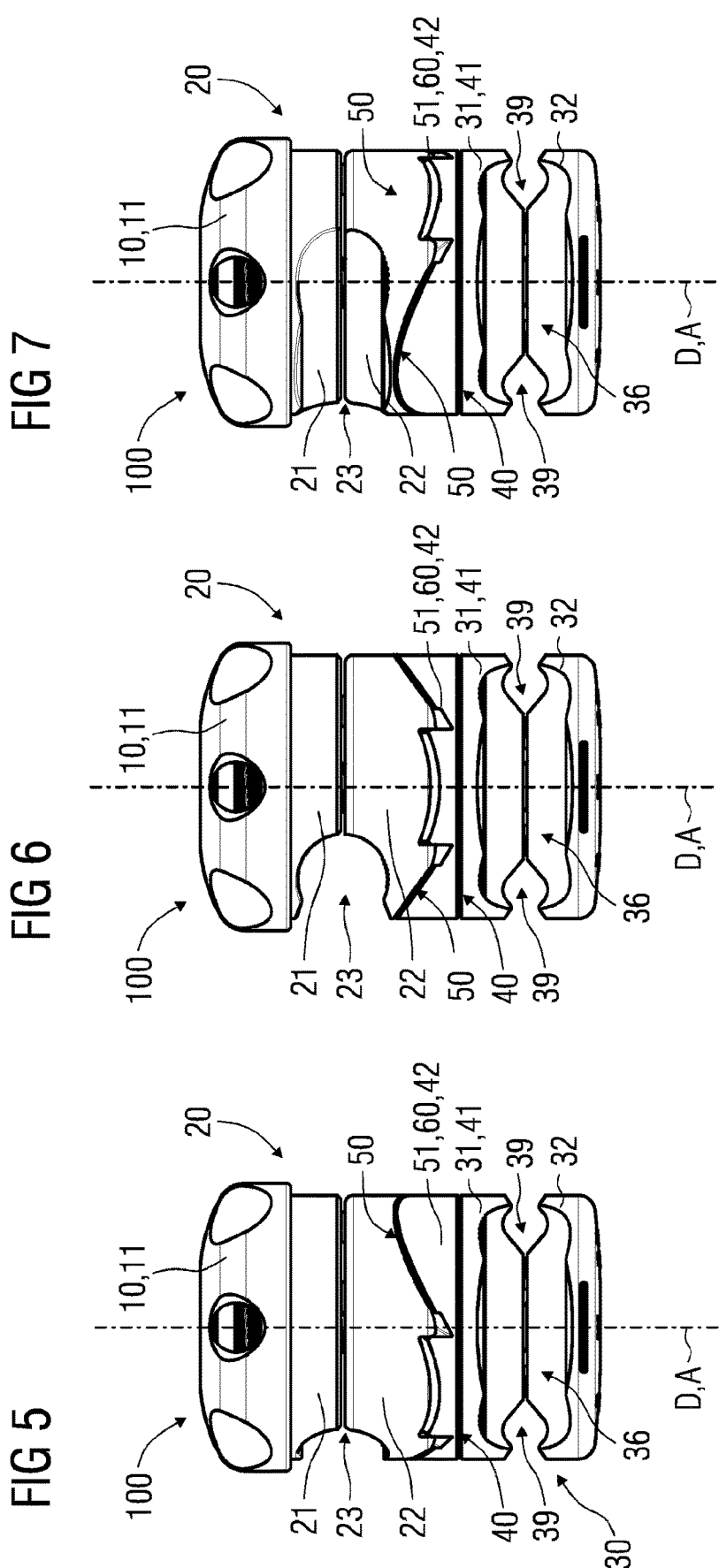
FIG. 5 shows the connecting apparatus of FIG. 1 in one possible spatial configuration, from the side.
FIG. 6 shows the connecting apparatus of FIG. 1 in a further possible spatial configuration, from the side.
FIG. 7 shows the connecting apparatus of FIG. 1 in a further possible spatial configuration, from the side.
Figure 8:
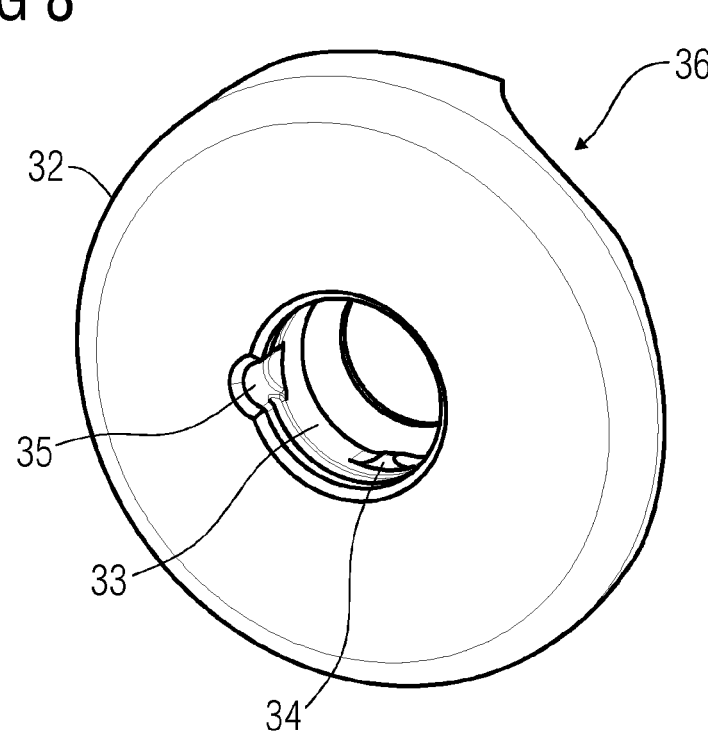
FIG. 8 shows a clamping jaw of the connecting apparatus of FIG. 1 in detail in a perspective view.

The first clamping arrangement 20 and the second clamping arrangement 30 can be locked in different angular positions with respect to the axis of rotation D and the pivot axis S by means of the tensile load acting along the traction means 83 in the axial direction A. FIGS. 2 to 4 show, by way of example, three different angular positions in which the first clamping arrangement 20 can be locked in different angular positions about the pivot axis S relative to the second clamping arrangement 30. Correspondingly, FIGS. 5 to 7 show, by way of example, three different angular positions in which the first clamping arrangement 20 can be locked in different angular positions about the axis of rotation D relative to the second clamping arrangement 30.

The rotary joint 40 comprises, as shown in particular in FIG. 1, two rotary joint components 41, 42 arranged opposite each other on end faces in the axial direction A, which are mounted facing each other and rotatable about the axis of rotation D. The traction means 80 is guided centrally through the rotary joint 40. For this purpose, the rotary joint components 41, 42 have central bores 43 in which the traction means 80 is inserted. The opposite end-face sides of the rotary joint components 41, 42 are also provided with first surface structures 44 (see in particular FIGS. 1 and 11), which are designed to be complementary to each other and provide a positive connection between the rotary joint components 41, 42. The first surface structures 44 substantially have toothed or corrugated structures. In the embodiment shown and not to be interpreted as limiting, the first surface structures 44 are designed as axially projecting, circumferential tooth structures, in particular with radial symmetry, which are arranged opposite each other and engage in each other with a positive connection when the rotary joint components 41, 42 are positioned in different angular positions with respect to the axis of rotation D and are locked by means of an axially acting force.

Figure 12:
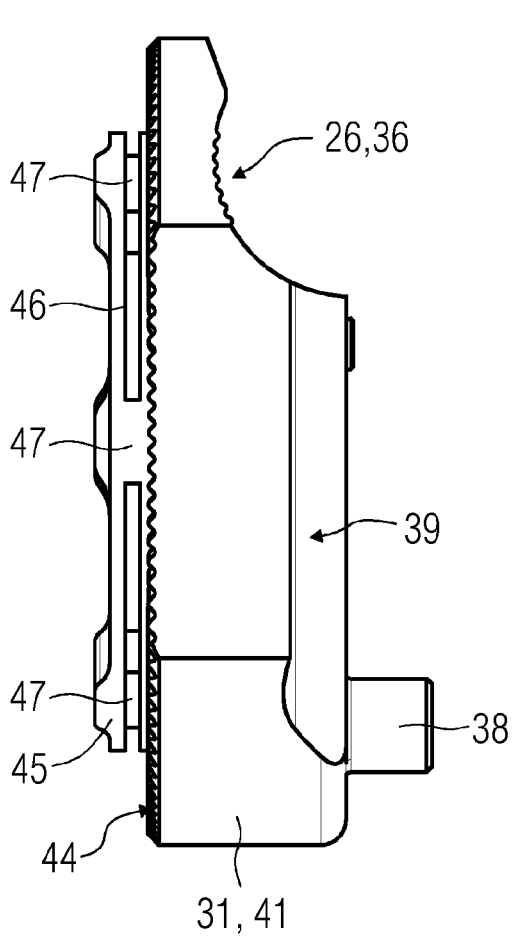
FIG. 12 shows the clamping jaw of FIG. 10 in a side view.
Figure 13:
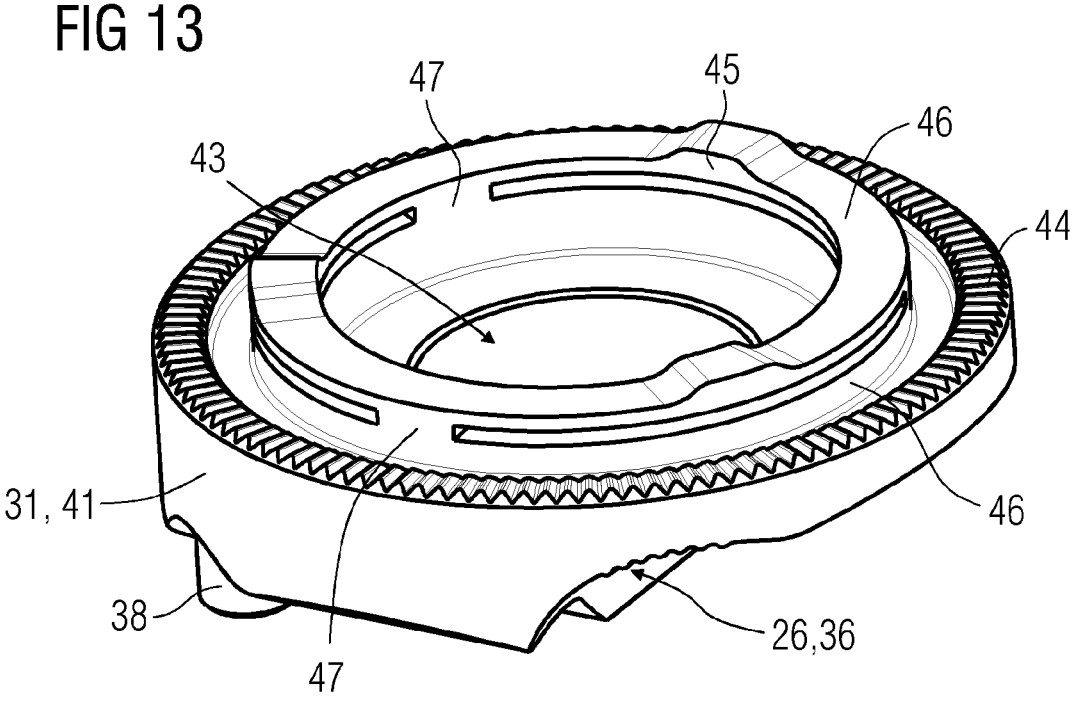
FIG. 13 shows the clamping jaw of FIG. 10 in a perspective view.

A first spring means 45 is arranged between the rotary joint components 41, 42 and is designed to resiliently load the rotary joint components 41, 42 against the tensile load that can be created by means of the traction means 80. The first spring means 45 is formed as a single piece with the rotary joint component 41 and protrudes from it in the axial direction A in the embodiment which is illustrated in FIGS. 12 and 13, and which is not to be considered restricting. The first spring means 45 is designed in particular to absorb transverse loads and forces in the axial direction A, and is designed to be deformable at least in some portions thereof. For this purpose, the first spring means 45 has a ring element 46 which is connected to the rotary joint component 41 via webs 47. Furthermore, the first spring means 45 prevents the first surface structures 44 of the two rotary joint components 41, 42 from snapping into each other in the event of an eccentric application of force—as can occur, for example, during the assembly of the connecting apparatus.

Figure 14:
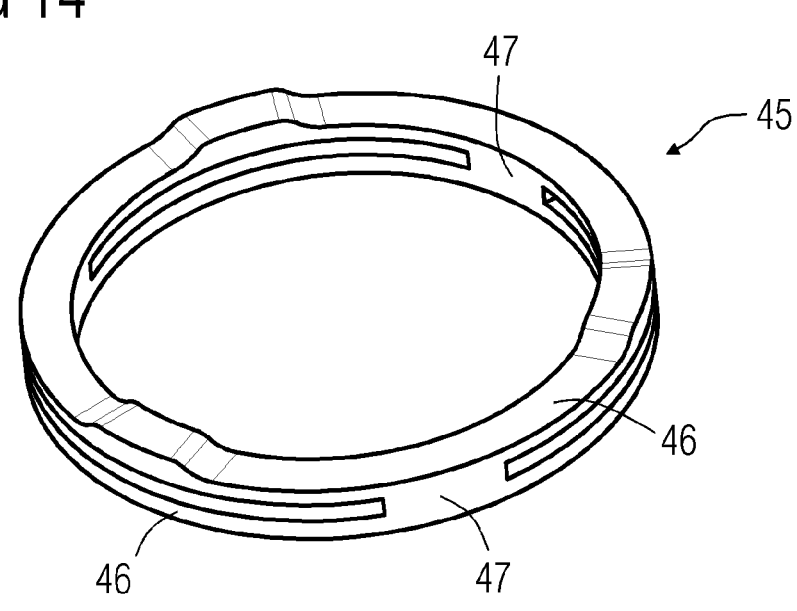
FIG. 14 shows a first spring means in a perspective view.
Figure 15:
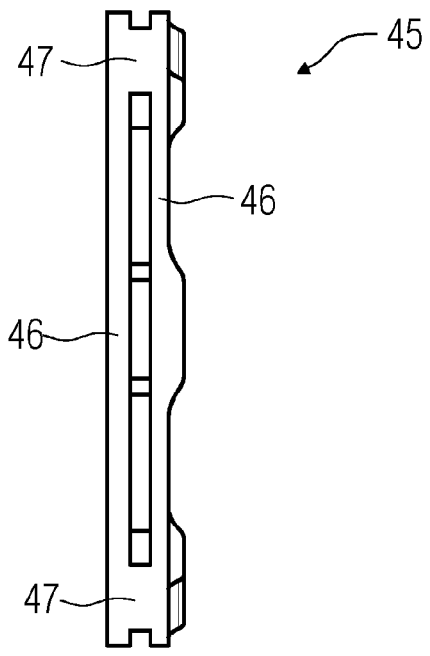
FIG. 15 shows the first spring means of FIG. 14 in a side view.

In alternative configurations, the first spring means 45 is implemented as a separate component (see FIGS. 14 and 15). For example, the first spring means 45 is designed as a wave spring and has two rings or ring elements 46 arranged concentrically to each other and around the axial direction A, which are connected to each other via axially running webs 47. The first spring means 45 can consist of titanium or aluminum, for example.

The rotary joint component 41 and the first clamping jaw 31 of the second clamping arrangement 30 are formed as a single piece in the illustrated and non-limiting embodiment. In alternative embodiments, the rotary joint component 41 and the first clamping jaw 31 are implemented as separate components, for example.

Figure 18:
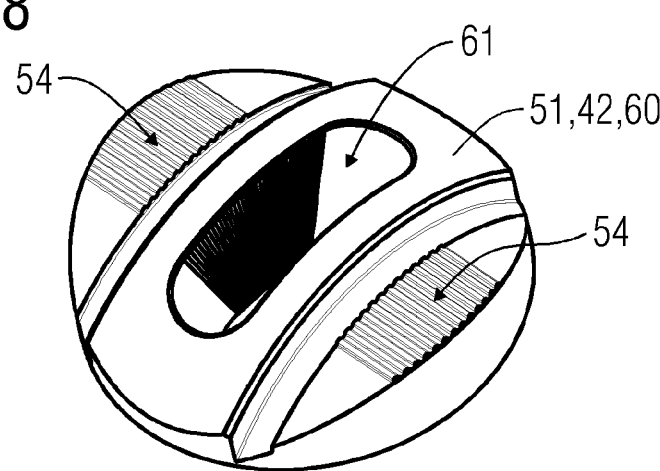
FIG. 18 shows a joint component of the connecting apparatus of FIG. 1 in a perspective view.
Figure 19:
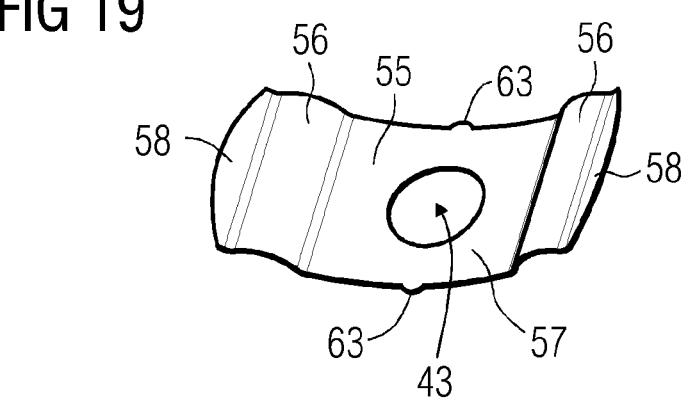
FIG. 19 shows a spring means designed as a leaf spring of the connecting apparatus of FIG. 1 in a perspective view.

In the embodiment shown and not to be interpreted as limiting, the rotary joint component 42 also forms a pivot joint component 51 of the pivot joint 50, and can therefore also be collectively referred to as a joint component 60, which is shown in a perspective view in FIG. 18. In alternative embodiments, the rotary joint component 42 and the pivot joint component 51 are implemented as separate components, for example.

The pivot joint 50 comprises two pivot joint components 51, 52 which are arranged opposite each other on end faces in the axial direction A, and which are mounted so that they can pivot relative to each other and about the pivot axis S. The traction means 80 is guided centrally through the pivot joint 40. The bore 43 in the pivot joint component 51 is designed as an elongated hole 61 (see in particular FIG. 18) which forms a kind of slotted link, along which the centrally guided traction means 80 is guided when the first and second clamping arrangements 20, 30 are moved relative to each other with respect to the pivot axis S. The pivot joint components 51, 52 and the clamping jaws 21, 22, 31, 32 are also provided with central bores 43 through which the traction means 80 is passed. The opposite sides of the pivot joint components 51, 52 are curved convexly or concavely in relation to the axial direction A, at least in certain areas, in such a way that the pivot joint components 51, 52 can be locked to each other with at least a non-positive and/or frictional connection with respect to the pivot axis S running perpendicular to the axis of rotation D. The radius of curvature of the convexly or concavely curved sections is in particular constant.

In the embodiment shown in the drawings, which is not to be interpreted as restrictive, the opposite sides of the pivot joint components 51, 52 are also provided with second surface structures 54 (see in particular FIGS. 17 and 18), which are designed to be complementary to each other and create a positive connection between the rotary joint components 51, 52. The second surface structures 54 substantially have toothed or corrugated structures. In the embodiment shown, which is not to be interpreted as limiting, the second surface structures 54 have a plurality of ribs and grooves which are designed to complement each other and are arranged parallel to each other and parallel to the pivot axis S. The second surface structures 54 engage in each other with a positive connection when the pivot joint components 51, 52 are positioned in different angular positions with respect to the pivot axis S in relation to each other.

A second spring means 55 is arranged between the pivot joint components 51, 52, which is designed to resiliently preload the pivot joint components 51, 52 against the tensile load that can be conveyed by means of the traction means 80. The second spring means 55 is designed in the form of a leaf spring in the embodiment shown, which is not to be interpreted as limiting, and has, as shown in particular in FIG. 19, a plurality of portions 56, 57, 58 which are differently curved relative to the axial direction A. The radially outer portions 56 are curved, for example, in the opposite direction to the central portion 57 and to the end portions 58, such that the spring force imparted by the second spring means 55 drives the pivot joint components 51, 52 apart in the axial direction A.

The second spring means 55 is arranged in a central region between the pivot joint components 51, 52 in the final assembled state. In the central region, the pivot joint component 51, as shown in particular in FIG. 18, is designed to be raised, for example. Correspondingly, the pivot joint component 52 has, for example, a depression 59 in the central region. Receptacles 62 are arranged on the edge of the depression 59 and are used to receive lateral projections 63 of the second spring means 55, such that it can be fixed in the central region between the pivot joint components 51, 52.

Figure 23:
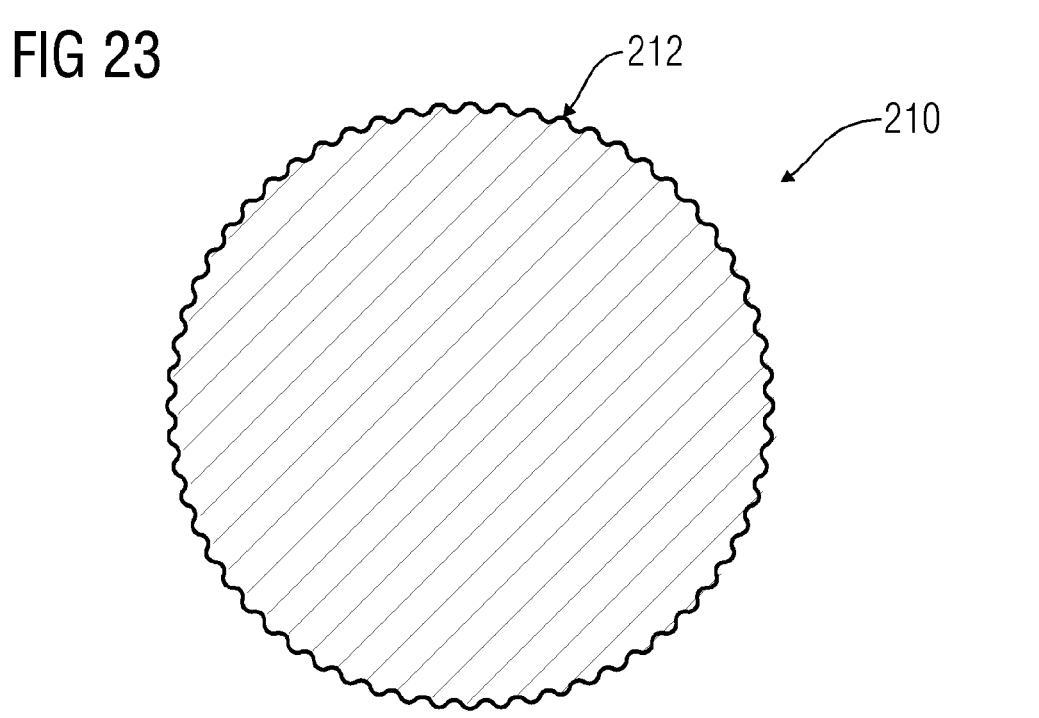
FIG. 23 shows a rod element in a sectional view.

FIG. 21 shows the external fixator 200 in a possible configuration for stabilizing a femoral fracture. A total of four pins 221 have been driven into the bone tissue of the femur. Two pins 220 are fastened to each connecting apparatus 100. The pins 220 are connected to each other via a rod element 210. The rod element 210 preferably has a fourth surface structure 212 which is complementary to the third surface structure 26, such that the rod element 210 is fixed in the receiving grooves 23, 36 in a non-positive and positive manner. Such a fourth surface structure 212 is designed, for example, in the form of a plurality of grooves, ridges and/or ridge-like ribs running parallel to each other, as illustrated in the embodiment in FIG. 23, which is not to be interpreted as limiting.

Figure 22:
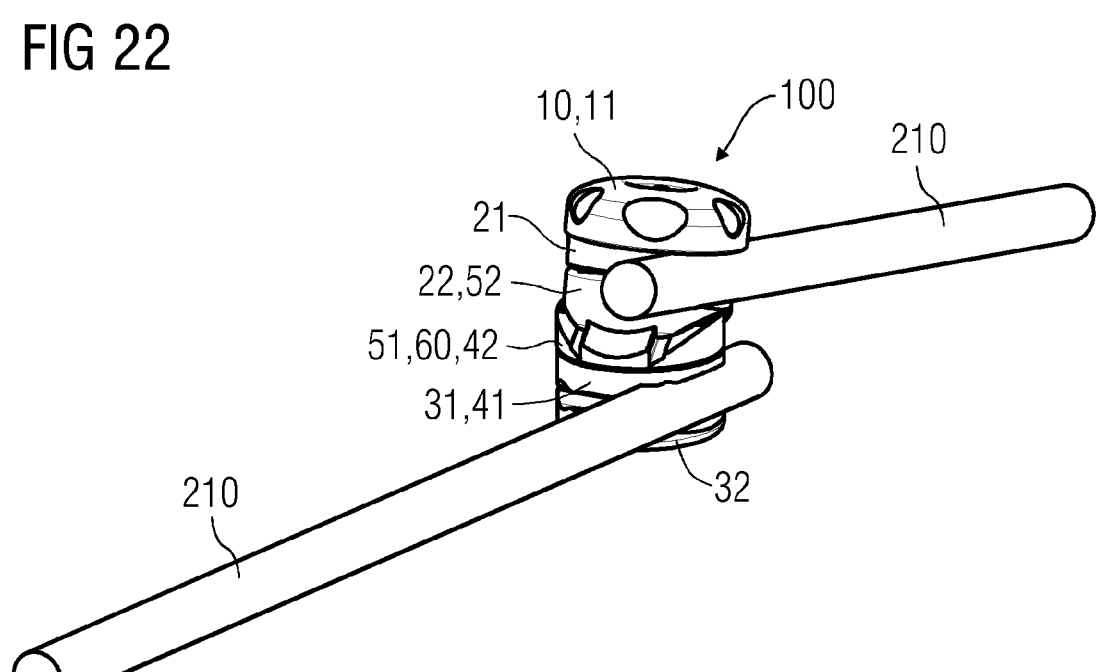
FIG. 22 shows two rod elements of the external fixator, which are connected to each other by means of a connecting apparatus according to FIG. 1, in a perspective view.

FIG. 22 shows a configuration in which two rod elements 210 have been connected to each other by means of a connecting apparatus 100. The rod elements 210, which in turn in particular have a fourth surface structure 212, are held in the first receiving grooves 23, 39 of the first and second clamping arrangements 20, 30 in a non-positive and positive manner. In the configuration shown as an example, the first and second clamping arrangements 20, 30 are adjusted relative to each other both with respect to the axis of rotation D and the pivot axis S. The second receiving grooves 39 for receiving pins 220 typically remain unused when two rod elements 210 are fastened to the connecting apparatus 100.

Figure 24:
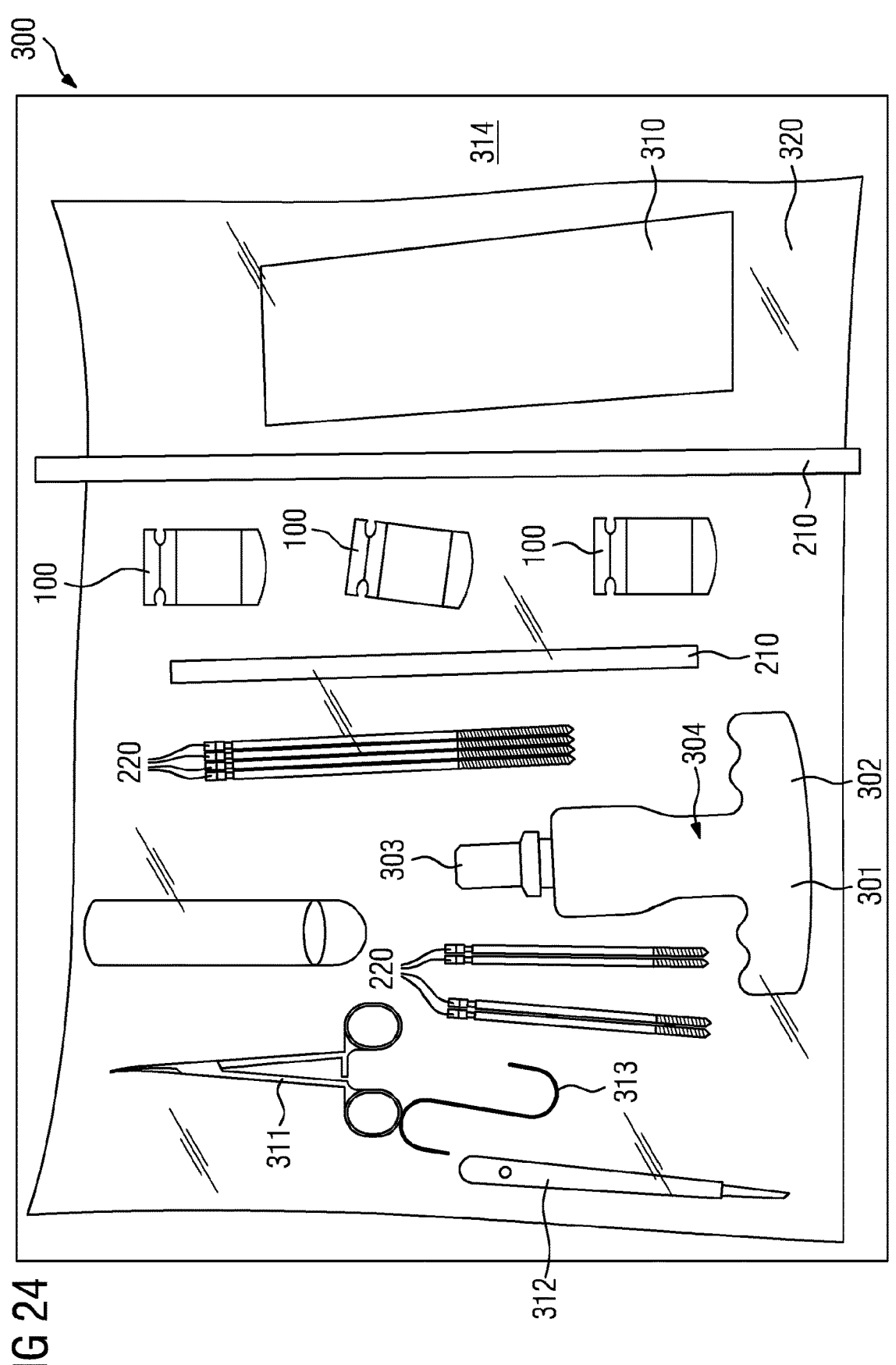
FIG. 24 shows an ambulatory emergency care device having a motor driven fastening device for driving pins into bone tissue of a patient.

FIG. 24 shows a device 300 for ambulatory emergency care, which has the components of the external fixator 200, i.e., in particular the connecting apparatuses 100 already described, rod elements 210 and pins 220, in particular pins 220 with different axial lengths and diameters, and other components that are necessary or helpful for the implementation of the emergency medical procedure. For this purpose, the device 300 comprises in particular a motor-driven fastening device 301 which is designed for screwing the pins 220 into bone tissue.

The fastening device 301 has a T-shaped grip 302 and is particularly designed for one-handed operated by a user. The fastening device 301 is designed as an electric screw driver and has a receptacle 303 in the manner of a chuck which is designed to non-positively fix, at the end on the grip 302, the pins 220 to be driven into the bone material of the bone parts to be immobilized. A disposable battery or a rechargeable battery, which is arranged inside the grip 302, is provided as the energy storage device 304 of the fastening device 301.

As additional components or medical accessories, the device 300 includes, for example, a wound dressing 310, a clamp 311, a scalpel 312 and an S-shaped hook 313, which can be used in particular to fasten infusion bags or the like. Furthermore, a cloth or a textile base 314 is included, on which the emergency medical procedure can be carried out in order to at least reduce the risk of contamination of the wound.

It goes without saying that this enumeration is not exhaustive and that further or other components for carrying out the emergency procedure within the framework of the device 300 for ambulatory emergency care may be included.

At least some of the components of the medical device 300, in particular those components that come into direct contact with the tissue of the injured person when performing the emergency procedure, such as the pins 220, the wound dressing 310 or the clamp 311, are preferably sealed in a welded plastic case 320 and are sterile.

The ambulatory emergency care of a fracture by means of the external fixator 200 is preferably carried out on the textile base 314, which is part of the device 300. First, the pins 220 must be driven into the bone fragments to be fixed. For this purpose, it may be necessary to create access through the surrounding muscle tissue, which can be done by means of the scalpel 312, for example. The clamp 311 can be used in particular to keep the access open in order to insert a tissue protection sleeve. An appropriate pin 220 is then inserted into the tissue protection sleeve and the pin 220 is driven in using the fastening device 301. In this case, the fastening device 301 is typically operated by a user with one hand, such that the other hand remains, if necessary, for immobilizing the injured part of the body. This process is repeated until a sufficient number of pins 220 has been driven into all of the bone fragments to be immobilized. The pins 220 connected to the bone parts are then connected to each other outside the patient's body via a suitable number of connecting apparatuses 100 and rod elements 210 in order to largely prevent movement of the bone fragments relative to each other and to enable the patient to be transported.

Figure 25:
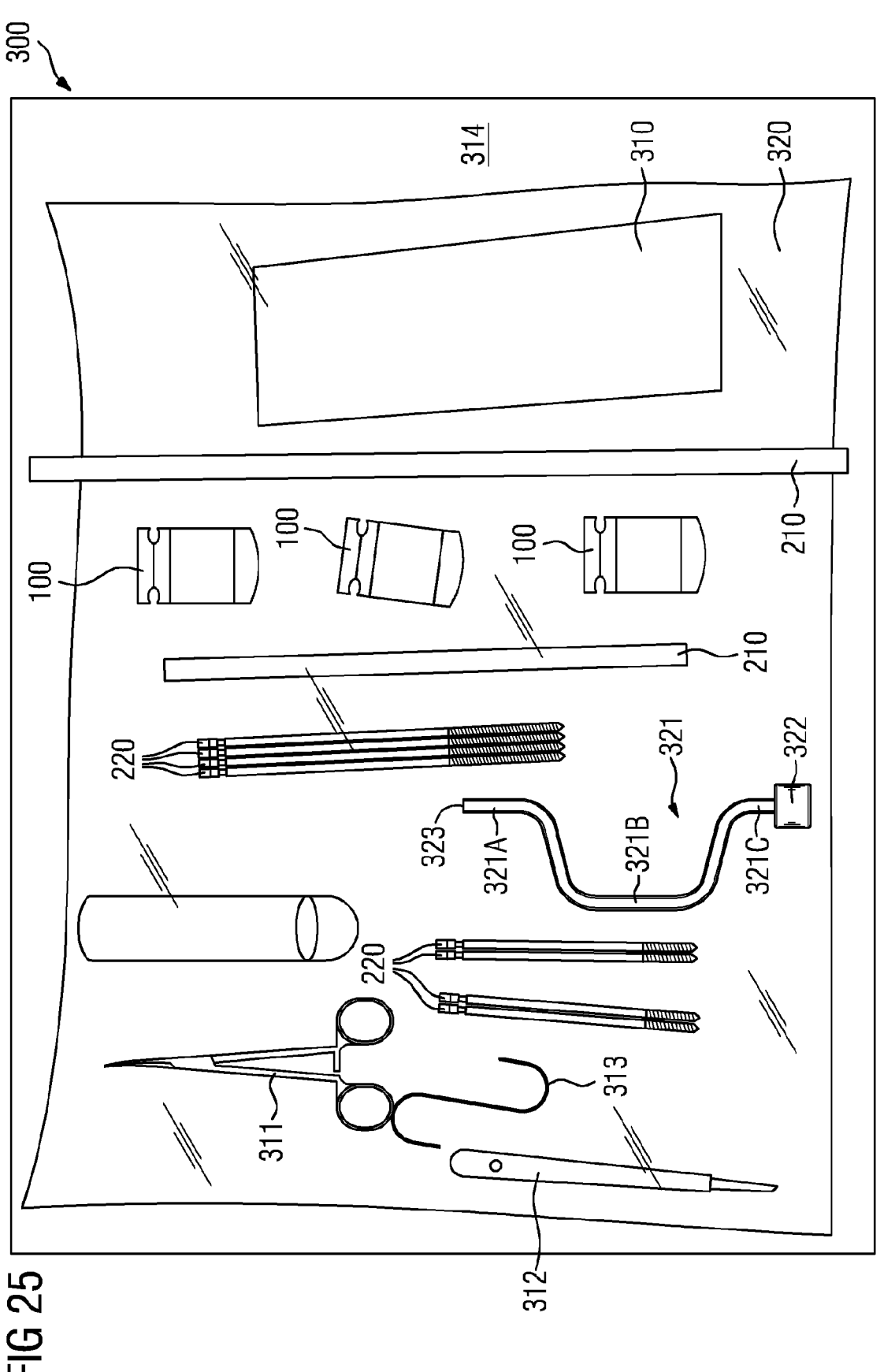
FIG. 25 shows a device for ambulatory emergency care with a manually drivable fastening device for driving pins into the bone tissue of a patient.

FIG. 25 shows a further embodiment of a device 300 for ambulatory emergency care, which has the components of the external fixator 200, i.e., in particular the connecting apparatuses 100 already described, rod elements 210 and pins 220, in particular pins 220 with different axial lengths and diameters, and other components that are necessary or helpful for the implementation of the emergency medical procedure. For this purpose, the device 300 comprises in particular a manually drivable fastening device 321 which is designed for screwing the pins 220 into bone tissue.

In the present case, the fastening device 321 is designed as a crank which has an offset axle with a front crank portion 321A, a middle crank portion 321B and a rear crank portion 321C. The front crank portion 321A and the rear crank portion 321C are oriented along an axis of rotation of the crank; the middle crank portion 321B is spaced from the axis of rotation. On the rear crank portion 321C, the fastening device 321 has a grip 322 in the form of a knob, in which the crank portion 321C is mounted so that it can rotate about the axis of rotation. On the front crank portion 321A, the fastening device 321 has a receptacle 323 in the form of a chuck, which is designed to non-positively fix, at the end on the grip 322, the pins 220 to be driven into the bone material of the bone parts to be fixed. In order to drive in the pins 220, the fastening device 321 is manually driven by rotating the central crank portion 321B about the axis of rotation.

Although the invention has been illustrated and described in detail with reference to the preferred embodiments, the invention is not limited thereby. Other variations and combinations can be derived from this by a person skilled in the art without departing from the essential idea of the invention. In particular, any combination of features that have been described or disclosed with reference to various embodiments and/or figures is possible.

For example, the second receiving grooves 39 for fastening pins 220 can alternatively be provided on the first clamping arrangement 20, or both the first clamping arrangement 20 and the second clamping arrangement 30 can be provided with second receiving grooves 39 for attaching pins 220. Variations in terms of the shape of the interlocking structures and/or the surface structures, in particular the first, second, third and/or fourth surface structures, are possible and intended.

LIST OF REFERENCE SIGNS

10 adjusting means
11 handwheel
15 spring
16 ring element
17 web
20 clamping arrangement
21 clamping jaw
22 clamping jaw
23 receiving groove
24 depression
25 pin
26 surface structure
30 clamping arrangement
31 clamping jaw
32 clamping jaw
33 joint socket
34 projection
35 groove
36 receiving groove
37 depression
38 pin
39 receiving groove
40 rotary joint
41 rotary joint component
42 rotary joint component
43 bore
44 surface structure
45 spring means
46 ring element
47 web
50 pivot joint
51 pivot joint component
52 pivot joint component
54 surface structure
55 spring means
56 portion
57 portion
58 portion
59 depression
60 joint component
61 elongated hole
62 receptacle
63 projection
70 joint
71 retaining ring
80 traction means
81 screw
82 external thread
83 head end

84 groove
85 internal thread
90 retaining screw
100 connecting apparatus
200 external fixator
210 rod element
212 surface structure
220 pin
221 tap thread
300 device
301 fastening device
302 grip
303 receptacle
304 energy storage device
310 wound dressing
311 clamp
312 scalpel
313 hook
314 base
320 plastic case
321 fastening device
323 receptacle
A axial direction
M central longitudinal axis
D axis of rotation
S pivot axis

The invention claimed is:

1. A connecting apparatus for the purpose of connecting pins and/or rod elements of an external fixator, having a first clamping arrangement for fastening at least one pin and/or rod element and a second clamping arrangement for fastening at least one pin and/or rod element, the first and second clamping arrangements being mounted to be rotatable relative to each other via a rotary joint about an axis of rotation and to be pivotable relative to each other via a pivot joint about a pivot axis which runs perpendicular to the axis of rotation characterized in that a traction means which can be subjected to a tensile load is guided through the first and second clamping arrangements, the rotary joint and the pivot joint, and is designed to fix the first and second clamping arrangement, and to lock them in different angular positions with respect to the axis of rotation and the pivot axis by creating a tensile force in the axial direction along the traction means;

wherein the connecting apparatus is characterized in that the rotary joint comprises at least two mutually adjoining rotary joint components which are mounted to be rotatable relative to each other about the axis of rotation, and which can be locked in different positions relative to each other by means of the traction means, wherein a first spring means, which is designed to brace the rotary joint components away from each other in the axial direction, is arranged between the rotary joint components and to absorb transverse loads and forces in the axial direction; and wherein the first spring means is formed as a single piece together with one of the rotary joint components, wherein the first spring means protrudes in the axial direction out of the rotary joint component.

2. The connecting apparatus according to claim 1, characterized in that the rotary joint components have first surface structures which are arranged opposite each other and are designed to complement each other, and which are designed to engage in each other with a positive connection in different angular positions.

3. The connecting apparatus according to claim 1, characterized in that the pivot joint comprises at least two mutually adjoining pivot joint components which are mounted pivotably relative to each other about the pivot axis, and which can be locked in different positions relative to each other by means of the traction means, wherein a second spring means, which is designed to brace the pivot joint components away from each other in the axial direction, is arranged between the pivot joint components.

4. The connecting apparatus according to claim 3, characterized in that the pivot joint components have second surface structures which are arranged opposite each other and which are designed to complement each other, and are designed to engage in each other with a positive connection in different angular positions.

5. The connecting apparatus according to claim 4, characterized in that the first clamping arrangement and/or the second clamping arrangement has two opposite first and second clamping jaws which can be braced against each other by the tensile force acting in the axial direction, and which each comprise oppositely arranged first receiving grooves for receiving a rod element.

6. The connecting apparatus according to claim 5, characterized in that the first receiving grooves are provided, at least in portions thereof, with third surface structures which are designed to positively engage in complementary surface structures of a rod element.

7. The connecting apparatus according to claim 6, characterized in that the first, second and/or third surface structures have a toothed or a corrugated structure.

8. The connecting apparatus according to claim 5, characterized in that the first and second clamping jaws are provided with interlocking structures which are designed to restrict or block rotation of the first and second clamping jaws.

9. The connecting apparatus according to claim 1, characterized in that the first clamping arrangement and/or second clamping arrangement has opposite first and second clamping jaws which can be braced against each other by the tensile force acting in the axial direction, each of which comprises oppositely arranged, second receiving grooves for receiving a pin.

10. The connecting apparatus according to claim 9, characterized in that the first and second clamping jaws have two second receiving grooves running parallel to each other, each for receiving a pin.

11. The connecting apparatus according to claim 1, characterized in that the traction means is movably guided at the end thereof in a joint, in particular a ball joint, of the connecting apparatus.

12. The connecting apparatus according to claim 11, characterized in that the traction means is designed as a screw with a head end which is at least partially spherical in shape, the head end being movably guided in a joint socket of the joint.

13. The connecting apparatus according to claim 12, characterized in that at least one groove is created in the head end of the screw, into which a projection protruding past the joint socket engages in such a way that rotation of the traction means about the axial direction is at least restricted.

14. An external fixator, comprising
at least two, in particular four, pins which are designed for anchoring, in particular by screwing, in bone tissue,
at least one rod element, in particular two rod elements, optionally with different axial lengths, and
at least one connecting apparatus, in particular at least two, for example three, connecting apparatuses, which are designed to mechanically connect at least one of the pins to the at least one rod element in particular, at least one connecting apparatus, in particular at least two, for example three, connecting apparatuses according to any of the preceding claims.

15. The external fixator according to claim 14, having at least one connecting apparatus and at least one rod element which has a surface structure designed to be complementary to a third surface structure.

16. A device for ambulatory emergency care, comprising at least the following components:
  an external fixator, in particular according to claim 14, having
  at least two, for example four, pins which are designed for anchoring, in particular by screwing, in bone tissue,
  at least one rod element, and
  at least one connecting apparatus, in particular at least two, for example three, connecting apparatuses, which are designed to mechanically connect at least one of the pins to the at least one rod element in particular, at least one connecting apparatus, in particular at least two, for example three, connecting apparatuses according to claim 1, characterized by
  a motor-driven fastening device for driving the pins into the bone tissue, the fastening device being designed for one-handed operation by a user, or
  a manually drivable fastening device for driving the pins into the bone tissue.

17. The device according to claim 16, wherein the motor-driven fastening device is designed as an electric screwdriver with a T-shaped grip.

18. The device according to claim 16, wherein the manually drivable fastening device is designed as a crank.

19. The device according to claim 18, wherein the crank has an offset axis, such that front and rear crank portions are oriented along an axis of rotation of the crank, and a central crank portion is spaced from the axis of rotation, and wherein the crank is manually driven or drivable by rotation of the central crank portion about the axis of rotation.

20. The device according to claim 16, wherein the fastening device has a receptacle for fastening one of the pins in a non-positive manner.

21. The device according to claim 16, wherein the fastening device has an energy storage device, in particular a disposable battery or a rechargeable battery.

22. The device according to claim 16, with at least two rod elements which optionally have different axial lengths, wherein the at least one connecting apparatus is designed to mechanically connect the at least two rod elements to each other.

23. The device according to claim 16, wherein at least two of the pins have different axial lengths and/or diameters.

24. The device according to claim 16, wherein at least some of the components of the device for ambulatory emergency care are sealed in a welded plastic case.

25. The device according to claim 24, wherein the components sealed in the welded plastic case are sterilized or can be sterilized.

26. A device according to claim 16, with a fabric base configured to be spread out on the ground in order to create an at least comparatively clean surgical environment for a procedure.

27. The device according to claim 16, wherein the at least one connecting apparatus is designed to mechanically connect the at least two pins to at least one of the rod elements.

28. The device according to claim 27, wherein the at least one connecting apparatus is designed to mechanically connect the at least two pins, in a parallel orientation, to at least one of the rod elements.

29. The device according claim 16, wherein the mechanical connection takes place by means of a positive connection which is created by mutually complementary surface structures.

* * * * *